(12) United States Patent
Fulkerson et al.

(10) Patent No.: US 10,035,103 B2
(45) Date of Patent: Jul. 31, 2018

(54) MODULAR, PORTABLE DIALYSIS SYSTEM

(75) Inventors: Barry Neil Fulkerson, Longmont, CO (US); Martin Hering, Irvine, CA (US); Mark F. Smith, Longmont, CO (US); Jan B. Zwierstra, San Pedro, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1664 days.

(21) Appl. No.: 12/610,032

(22) Filed: Oct. 30, 2009

(65) Prior Publication Data

US 2010/0140149 A1 Jun. 10, 2010

Related U.S. Application Data

(60) Provisional application No. 61/109,834, filed on Oct. 30, 2008.

(51) Int. Cl.
*B01D 61/28* (2006.01)
*A61M 1/14* (2006.01)

(52) U.S. Cl.
CPC .............. *B01D 61/28* (2013.01); *A61M 1/14* (2013.01); *A61M 2205/121* (2013.01); *A61M 2205/3569* (2013.01); *A61M 2209/084* (2013.01); *B01D 2313/20* (2013.01)

(58) Field of Classification Search
CPC .................................................. B01D 61/28
USPC .................................... 210/645, 646; 604/29
See application file for complete search history.

(56) References Cited

U.S. PATENT DOCUMENTS 2,328,381 A 8/1943 Jaffe
3,242,456 A * 3/1966 Duncan .......................... 439/252
3,388,803 A 6/1968 Scott
3,709,222 A 1/1973 De Vries
3,746,175 A 7/1973 Markley
3,803,913 A 4/1974 Tracer
3,814,376 A 6/1974 Reinicke
3,884,808 A 5/1975 Scott
3,894,431 A 7/1975 Muston
3,902,490 A 9/1975 Jacobsen
3,946,731 A 3/1976 Lichtenstein
3,961,918 A 6/1976 Johnson
3,989,622 A 11/1976 Marantz
(Continued)

FOREIGN PATENT DOCUMENTS

CN 1471617 A 1/2004
EP 0808633 11/1997
(Continued)

OTHER PUBLICATIONS

International Search Report for PCT/US08/85062, dated Jun. 11, 2009, XCorporeal, Inc.
(Continued)

*Primary Examiner* — Peter Keyworth
(74) *Attorney, Agent, or Firm* — Novel IP

(57) ABSTRACT

The present invention is directed toward a dialysis unit that is modular and portable, with improved functionality. In one embodiment, the dialysis system comprises a top unit that is detachably affixed to a base that comprises a reservoir for fluid storage. Among numerous other features, the portable, modular dialysis system of the present invention has improved power door locking, zoned leak detection, fluid handling, and mechanical design features that enable improved modularity.

11 Claims, 16 Drawing Sheets

(56) References Cited

U.S. PATENT DOCUMENTS

| | | |
|---|---|---|
| 3,989,625 A | 11/1976 | Mason |
| 3,994,799 A | 11/1976 | Yao |
| 4,000,072 A | 12/1976 | Sato |
| 4,071,444 A | 1/1978 | Ash et al. |
| 4,083,777 A | 4/1978 | Hutchisson |
| 4,094,775 A | 6/1978 | Mueller |
| 4,113,614 A | 9/1978 | Rollo |
| 4,118,314 A | 10/1978 | Yoshida |
| 4,209,392 A | 6/1980 | Wallace |
| 4,212,738 A | 7/1980 | Henne |
| 4,247,393 A | 1/1981 | Wallace |
| 4,267,040 A | 5/1981 | Schael |
| 4,269,708 A | 5/1981 | Bonomini |
| 4,326,955 A | 4/1982 | Babb |
| 4,348,283 A | 9/1982 | Ash |
| 4,354,562 A | 10/1982 | Newman |
| 4,368,737 A | 1/1983 | Ash |
| 4,387,777 A | 6/1983 | Ash |
| 4,397,189 A | 8/1983 | Johnson |
| 4,397,519 A * | 8/1983 | Cooney ............... 439/824 |
| 4,402,694 A | 9/1983 | Ash et al. |
| 4,403,765 A | 9/1983 | Fisher |
| 4,403,984 A | 9/1983 | Ash et al. |
| 4,413,988 A | 11/1983 | Handt et al. |
| 4,430,098 A | 2/1984 | Bowman |
| 4,443,333 A | 4/1984 | Mahurkar |
| 4,464,172 A | 8/1984 | Lichtenstein |
| 4,466,804 A | 8/1984 | Hino |
| 4,469,593 A | 9/1984 | Ishihara et al. |
| 4,477,342 A | 10/1984 | Allan |
| 4,480,483 A | 11/1984 | McShane |
| 4,498,902 A | 2/1985 | Ash et al. |
| 4,531,799 A * | 7/1985 | Gray ............... 439/298 |
| 4,535,637 A | 8/1985 | Feller |
| 4,559,039 A | 12/1985 | Ash et al. |
| 4,563,170 A | 1/1986 | Aigner |
| 4,581,141 A | 4/1986 | Ash |
| 4,596,550 A | 6/1986 | Troutner |
| 4,599,055 A | 7/1986 | Dykstra |
| 4,606,826 A | 8/1986 | Sano |
| 4,630,799 A | 12/1986 | Nolan |
| 4,661,246 A | 4/1987 | Ash |
| 4,666,598 A | 5/1987 | Heath |
| 4,680,122 A | 7/1987 | Barone |
| 4,683,053 A | 7/1987 | Polaschegg |
| 4,710,164 A | 12/1987 | Levin |
| 4,740,755 A | 4/1988 | Ogawa |
| 4,750,705 A | 6/1988 | Zippe |
| 4,762,618 A | 8/1988 | Gummesson |
| 4,765,907 A | 8/1988 | Scott |
| 4,777,953 A | 10/1988 | Ash et al. |
| 4,806,247 A | 2/1989 | Schoendorfer |
| 4,828,543 A | 5/1989 | Weiss |
| 4,831,884 A | 5/1989 | Drenthen |
| 4,854,322 A | 8/1989 | Ash et al. |
| 4,861,242 A | 8/1989 | Finsterwald |
| 4,885,942 A | 12/1989 | Magori |
| 4,897,189 A | 1/1990 | Greenwood |
| 4,909,713 A | 3/1990 | Finsterwald |
| 4,914,819 A | 4/1990 | Ash |
| 4,943,279 A | 7/1990 | Samiotes |
| 4,950,244 A | 8/1990 | Fellingham |
| 4,950,395 A | 8/1990 | Richalley |
| 4,968,422 A | 11/1990 | Runge |
| 4,990,258 A | 2/1991 | Bjare |
| 4,995,268 A | 2/1991 | Ash et al. |
| 4,997,570 A | 3/1991 | Polaschegg |
| 5,002,054 A | 3/1991 | Ash et al. |
| 5,011,607 A | 4/1991 | Shinzato |
| 5,032,261 A | 7/1991 | Pyper |
| 5,074,368 A | 12/1991 | Bullivant |
| 5,100,554 A | 3/1992 | Polaschegg |
| 5,114,580 A | 5/1992 | Ahmad et al. |
| 5,147,613 A | 9/1992 | Heilmann et al. |
| 5,152,174 A | 10/1992 | Labudde |
| 5,157,332 A | 10/1992 | Reese |
| 5,161,779 A | 11/1992 | Graner |
| 5,170,789 A | 12/1992 | Narayan |
| 5,198,335 A | 3/1993 | Sekikawa et al. |
| 5,211,643 A | 5/1993 | Reinhardt et al. |
| 5,215,450 A | 6/1993 | Tamari |
| 5,228,308 A | 7/1993 | Day |
| 5,230,341 A | 7/1993 | Polaschegg |
| 5,230,614 A | 7/1993 | Zanger |
| 5,258,127 A | 11/1993 | Gsell |
| 5,277,820 A | 1/1994 | Ash |
| 5,284,470 A | 2/1994 | Beltz |
| 5,284,559 A | 2/1994 | Lim |
| 5,295,505 A | 3/1994 | Polaschegg et al. |
| 5,304,349 A | 4/1994 | Polaschegg |
| 5,308,315 A | 5/1994 | Khuri et al. |
| 5,322,258 A | 6/1994 | Bosch |
| 5,322,519 A | 6/1994 | Ash |
| 5,346,472 A | 9/1994 | Keshaviah |
| 5,360,445 A | 11/1994 | Goldowsky |
| 5,385,005 A | 1/1995 | Ash |
| 5,391,143 A | 2/1995 | Kensey |
| 5,405,315 A | 4/1995 | Khuri et al. |
| 5,405,320 A | 4/1995 | Twardowski |
| 5,415,532 A | 5/1995 | Loughnane |
| 5,441,636 A | 8/1995 | Chevallet |
| 5,445,630 A | 8/1995 | Richmond |
| 5,460,493 A | 10/1995 | Deniega et al. |
| D355,816 S | 12/1995 | Ash |
| 5,476,444 A | 12/1995 | Keeling et al. |
| D370,531 S | 6/1996 | Ash et al. |
| 5,536,412 A | 7/1996 | Ash |
| 5,540,265 A | 7/1996 | Polaschegg et al. |
| 5,545,131 A | 8/1996 | Davankov |
| 5,577,891 A | 11/1996 | Loughnane et al. |
| 5,580,460 A | 12/1996 | Polaschegg |
| 5,609,770 A | 3/1997 | Zimmerman |
| 5,614,677 A | 3/1997 | Wamsiedler et al. |
| 5,629,871 A | 3/1997 | Love |
| 5,616,305 A | 4/1997 | Mathieu |
| 5,624,551 A | 4/1997 | Baumann et al. |
| 5,632,897 A | 5/1997 | Mathieu |
| 5,644,285 A | 7/1997 | Maurer |
| 5,674,390 A | 10/1997 | Matthews |
| 5,679,245 A | 10/1997 | Manica |
| 5,693,008 A | 12/1997 | Brugger |
| 5,698,083 A | 12/1997 | Glass |
| 5,711,883 A | 1/1998 | Folden et al. |
| 5,713,850 A | 2/1998 | Heilmann et al. |
| 5,725,773 A | 3/1998 | Polaschegg |
| 5,725,776 A | 3/1998 | Kenley et al. |
| 5,744,027 A | 4/1998 | Connell |
| 5,770,806 A | 6/1998 | Hiismaeki |
| 5,782,796 A | 7/1998 | Din et al. |
| 5,794,669 A | 8/1998 | Polaschegg et al. |
| 5,840,068 A | 11/1998 | Cartledge |
| 5,858,186 A | 1/1999 | Glass |
| 5,876,419 A | 3/1999 | Carpenter |
| 5,902,336 A | 5/1999 | Mishkin |
| 5,906,978 A | 5/1999 | Ash |
| 5,919,369 A | 7/1999 | Ash |
| 5,938,938 A | 8/1999 | Bosetto |
| 5,944,684 A | 8/1999 | Roberts |
| 5,945,343 A | 8/1999 | Munkholm |
| 5,947,953 A | 9/1999 | Ash et al. |
| 5,951,870 A | 9/1999 | Utterberg |
| 5,980,481 A | 11/1999 | Gorsuch |
| 5,984,891 A | 11/1999 | Keilman |
| 5,989,423 A | 11/1999 | Kamen |
| 5,989,438 A | 11/1999 | Fumiyama |
| 6,042,561 A | 3/2000 | Ash et al. |
| 6,044,691 A * | 4/2000 | Kenley et al. ............. 73/40.5 R |
| 6,086,753 A | 7/2000 | Ericson |
| 6,117,100 A | 9/2000 | Powers |
| 6,117,122 A | 9/2000 | Din |
| 6,156,007 A | 12/2000 | Ash |
| 6,168,578 B1 | 1/2001 | Diamond |
| 6,190,349 B1 | 2/2001 | Ash et al. |
| 6,196,922 B1 | 3/2001 | Hantschk |

(56) References Cited

U.S. PATENT DOCUMENTS

| | | |
|---|---|---|
| 6,196,992 B1 | 3/2001 | Keilman |
| 6,200,485 B1 | 3/2001 | Kitaevich |
| 6,217,540 B1 | 4/2001 | Yazawa et al. |
| 6,234,989 B1 | 5/2001 | Brierton et al. |
| 6,254,567 B1 | 7/2001 | Treu et al. |
| 6,264,611 B1 | 7/2001 | Ishikawa |
| 6,264,680 B1 | 7/2001 | Ash |
| 6,280,406 B1 | 8/2001 | Dolcek |
| 6,284,131 B1 | 9/2001 | Hogard |
| 6,287,516 B1 | 9/2001 | Matson et al. |
| 6,303,036 B1 | 10/2001 | Collins et al. |
| 6,325,774 B1 | 12/2001 | Bene |
| 6,332,985 B1 | 12/2001 | Sherman et al. |
| 6,348,162 B1 | 2/2002 | Ash |
| 6,406,631 B1 | 6/2002 | Collins |
| 6,409,699 B1 | 6/2002 | Ash |
| 6,416,293 B1 | 7/2002 | Bouchard |
| 6,468,427 B1 | 10/2002 | Frey |
| 6,471,872 B2 | 10/2002 | Kitaevich et al. |
| 6,487,904 B1 | 12/2002 | Myhre |
| 6,491,656 B1 | 12/2002 | Morris |
| 6,491,673 B1 | 12/2002 | Palumbo |
| 6,497,675 B1 | 12/2002 | Davankov |
| 6,517,045 B1 | 2/2003 | Northedge |
| 6,551,513 B2 | 4/2003 | Nikaido et al. |
| 6,554,789 B1 | 4/2003 | Brugger et al. |
| 6,561,997 B1 | 5/2003 | Weitzel |
| 6,572,576 B2 | 6/2003 | Brugger et al. |
| 6,572,641 B2 | 6/2003 | Brugger et al. |
| 6,579,253 B1 | 6/2003 | Burbank et al. |
| 6,579,460 B1 | 6/2003 | Willis et al. |
| 6,582,385 B2 | 6/2003 | Burbank et al. |
| 6,589,482 B1 | 7/2003 | Burbank et al. |
| 6,595,943 B1 | 7/2003 | Burbank |
| 6,607,495 B1 * | 8/2003 | Skalak et al. ............... 600/573 |
| 6,610,036 B2 | 8/2003 | Branch |
| 6,623,470 B2 | 9/2003 | Munis et al. |
| 6,627,164 B1 | 9/2003 | Wong |
| 6,632,192 B2 | 10/2003 | Gorsuch |
| 6,638,477 B1 | 10/2003 | Treu et al. |
| 6,638,478 B1 | 10/2003 | Treu et al. |
| 6,649,063 B2 | 11/2003 | Brugger et al. |
| 6,653,841 B1 | 11/2003 | Koerdt et al. |
| 6,673,314 B1 | 1/2004 | Burbank et al. |
| 6,681,624 B2 | 1/2004 | Furuki |
| 6,685,664 B2 | 2/2004 | Levin |
| 6,690,280 B2 | 2/2004 | Citrenbaum |
| 6,695,803 B1 | 2/2004 | Robinson |
| 6,702,561 B2 | 3/2004 | Stillig et al. |
| 6,706,007 B2 | 3/2004 | Gelfand |
| 6,730,266 B2 | 5/2004 | Matson et al. |
| 6,743,193 B2 | 6/2004 | Brugger et al. |
| 6,758,975 B2 | 7/2004 | Peabody |
| 6,764,460 B2 | 7/2004 | Dolecek et al. |
| 6,773,412 B2 | 8/2004 | OMahony et al. |
| 6,776,912 B2 | 8/2004 | Baurmeister |
| 6,796,955 B2 | 9/2004 | OMahony et al. |
| 6,818,196 B2 | 11/2004 | Wong |
| 6,830,553 B1 | 12/2004 | Burbank et al. |
| 6,836,201 B1 | 12/2004 | Devenyi |
| 6,841,172 B1 | 1/2005 | Ash |
| 6,843,779 B1 | 1/2005 | Andrysiak |
| 6,852,090 B2 | 2/2005 | Burbank et al. |
| 6,872,346 B2 | 3/2005 | Stillig |
| 6,878,283 B2 | 4/2005 | Thompson |
| 6,890,315 B1 | 5/2005 | Levin |
| 6,899,691 B2 | 5/2005 | Bainbridge |
| 6,923,782 B2 | 8/2005 | O'Mahony et al. |
| 6,948,697 B2 | 9/2005 | Herbert |
| 6,955,655 B2 | 10/2005 | Burbank et al. |
| 6,958,049 B1 | 10/2005 | Ash |
| 6,960,179 B2 | 11/2005 | Gura |
| 6,960,328 B2 | 11/2005 | Bortun et al. |
| 6,979,309 B2 | 12/2005 | Burbank et al. |
| 7,004,924 B1 | 2/2006 | Brugger et al. |
| 7,007,549 B2 | 3/2006 | Kwon |
| 7,033,498 B2 | 4/2006 | Wong |
| 7,040,142 B2 | 5/2006 | Burbank |
| 7,087,026 B2 | 8/2006 | Callister |
| 7,087,033 B2 | 8/2006 | Brugger et al. |
| 7,101,519 B2 | 9/2006 | Wong |
| 7,112,273 B2 | 9/2006 | Weigel et al. |
| 7,115,095 B2 | 10/2006 | Eigler et al. |
| 7,135,156 B2 | 11/2006 | Hai et al. |
| 7,144,386 B2 | 12/2006 | Korkor et al. |
| 7,147,613 B2 | 12/2006 | Burbank et al. |
| 7,169,303 B2 | 1/2007 | Sullivan et al. |
| 7,175,809 B2 | 2/2007 | Gelfand et al. |
| 7,214,312 B2 | 5/2007 | Brugger et al. |
| 7,226,538 B2 | 6/2007 | Brugger et al. |
| 7,241,272 B2 | 7/2007 | Karoor et al. |
| 7,252,767 B2 | 8/2007 | Bortun et al. |
| 7,267,658 B2 | 9/2007 | Treu et al. |
| 7,270,015 B1 | 9/2007 | Feller |
| 7,273,465 B2 | 9/2007 | Ash |
| 7,276,042 B2 | 10/2007 | Polaschegg et al. |
| 7,300,413 B2 | 11/2007 | Burbank et al. |
| 7,309,323 B2 | 12/2007 | Gura et al. |
| 7,314,208 B1 | 1/2008 | Rightley |
| 7,317,967 B2 | 1/2008 | DiGianfilippo et al. |
| 7,332,096 B2 | 2/2008 | Blickhan |
| 7,337,674 B2 | 3/2008 | Burbank et al. |
| 7,338,460 B2 | 3/2008 | Burbank et al. |
| 7,347,849 B2 | 3/2008 | Brugger et al. |
| 7,351,218 B2 | 4/2008 | Bene |
| 7,387,022 B1 | 6/2008 | Korniyenko |
| 7,494,590 B2 | 2/2009 | Felding et al. |
| 7,531,098 B2 | 5/2009 | Robinson |
| 7,597,677 B2 | 10/2009 | Gura |
| 7,605,710 B2 | 10/2009 | Crnkovich |
| 7,618,531 B2 | 11/2009 | Sugioka |
| 7,628,378 B2 | 12/2009 | Adams |
| 7,645,253 B2 | 1/2010 | Gura |
| 7,648,476 B2 | 1/2010 | Bock |
| 7,696,762 B2 | 4/2010 | Quackenbush |
| 7,713,226 B2 | 5/2010 | Ash |
| 7,755,488 B2 | 7/2010 | Dvorsky |
| 7,780,619 B2 | 8/2010 | Brugger |
| 7,794,141 B2 | 9/2010 | Perry |
| 7,873,489 B2 | 1/2011 | Dolgos |
| 7,874,999 B2 | 1/2011 | Busby |
| 7,886,611 B2 | 2/2011 | OMahony et al. |
| 7,896,829 B2 | 3/2011 | Gura |
| 7,901,376 B2 | 3/2011 | Steck et al. |
| 7,922,898 B2 | 4/2011 | Jonsson |
| 7,922,899 B2 | 4/2011 | Vasta |
| 7,935,074 B2 | 5/2011 | Plahey |
| 7,959,129 B2 | 6/2011 | Matsumoto |
| 7,981,280 B2 | 7/2011 | Carr |
| 7,995,816 B2 | 8/2011 | Roger |
| 7,998,101 B2 | 8/2011 | Ash |
| 8,021,319 B2 | 9/2011 | Delnevo |
| 8,029,454 B2 | 10/2011 | Kelly |
| 8,034,235 B2 | 10/2011 | Rohde |
| 8,062,513 B2 | 11/2011 | Yu |
| 8,066,658 B2 | 11/2011 | Karoor |
| 8,070,707 B2 | 12/2011 | Gelfand |
| 8,075,509 B2 | 12/2011 | Molducci |
| 8,078,333 B2 | 12/2011 | Kienman |
| 8,083,677 B2 | 12/2011 | Rohde |
| 8,105,260 B2 | 1/2012 | Tonelli |
| 8,105,487 B2 | 1/2012 | Fulkerson |
| 8,114,288 B2 | 2/2012 | Robinson |
| 8,152,751 B2 | 2/2012 | Roger |
| 8,142,383 B2 | 3/2012 | Dannenmaier |
| 8,187,184 B2 | 5/2012 | Muller |
| 8,197,431 B2 | 6/2012 | Bennison |
| 8,221,320 B2 | 7/2012 | Bouton |
| 8,376,978 B2 | 2/2013 | Roger |
| 2002/0068364 A1 | 6/2002 | Arai et al. |
| 2002/0085951 A1 | 7/2002 | Gelfand et al. |
| 2002/0112609 A1 | 8/2002 | Wong |
| 2002/0113016 A1 | 8/2002 | Takai |
| 2002/0147423 A1 | 10/2002 | Burbank |

(56) References Cited

U.S. PATENT DOCUMENTS

| | | |
|---|---|---|
| 2002/0187069 A1 | 12/2002 | Levin |
| 2003/0012905 A1 | 1/2003 | Zumbrum |
| 2003/0048185 A1 | 3/2003 | Citrenbaum |
| 2003/0056585 A1 | 3/2003 | Furuki |
| 2003/0113931 A1 | 6/2003 | Pan et al. |
| 2003/0113932 A1 | 6/2003 | Sternberg et al. |
| 2003/0128125 A1 | 7/2003 | Burbank |
| 2003/0216677 A1 | 11/2003 | Pan et al. |
| 2003/0236482 A1 | 12/2003 | Gorsuch |
| 2004/0021108 A1 | 2/2004 | Hallback |
| 2004/0031756 A1* | 2/2004 | Suzuki et al. ............ 210/646 |
| 2004/0167465 A1 | 8/2004 | Mihai |
| 2005/0070837 A1 | 3/2005 | Ferrarini et al. |
| 2005/0086008 A1 | 4/2005 | Digianfilippo |
| 2005/0131332 A1 | 6/2005 | Kelly et al. |
| 2005/0133439 A1 | 6/2005 | Blickhan |
| 2005/0150309 A1 | 7/2005 | Beard |
| 2005/0240233 A1 | 10/2005 | Lippert |
| 2006/0064053 A1 | 3/2006 | Bollish |
| 2006/0122552 A1 | 6/2006 | O'Mahony |
| 2006/0195064 A1* | 8/2006 | Plahey et al. ............ 604/151 |
| 2006/0226057 A1 | 10/2006 | Robinson |
| 2006/0241543 A1 | 10/2006 | Gura |
| 2006/0289342 A1 | 12/2006 | Sugioka |
| 2007/0060786 A1 | 3/2007 | Gura |
| 2007/0112297 A1 | 5/2007 | Plahey et al. |
| 2007/0158249 A1 | 7/2007 | Ash |
| 2007/0158268 A1 | 7/2007 | DeComo |
| 2007/0161113 A1 | 7/2007 | Ash |
| 2007/0179425 A1 | 8/2007 | Gura |
| 2007/0213654 A1 | 9/2007 | Lundtveit et al. |
| 2007/0276328 A1 | 11/2007 | Childers |
| 2008/0006570 A1 | 1/2008 | Gura |
| 2008/0021366 A1 | 1/2008 | Gura |
| 2008/0041136 A1 | 2/2008 | Kopelman et al. |
| 2008/0041792 A1 | 2/2008 | Crnkovich et al. |
| 2008/0051689 A1 | 2/2008 | Gura |
| 2008/0058696 A1 | 3/2008 | Gura |
| 2008/0065006 A1 | 3/2008 | Roger |
| 2008/0149563 A1 | 6/2008 | Ash |
| 2008/0195021 A1 | 8/2008 | Roger |
| 2008/0195060 A1 | 8/2008 | Roger |
| 2008/0208103 A1* | 8/2008 | Demers et al. ........... 604/6.11 |
| 2008/0217245 A1 | 9/2008 | Rambod |
| 2008/0230450 A1 | 9/2008 | Burbank et al. |
| 2008/0258735 A1 | 10/2008 | Quackenbush et al. |
| 2008/0264498 A1 | 10/2008 | Thompson |
| 2008/0290974 A1 | 11/2008 | Adams |
| 2009/0004053 A1 | 1/2009 | Kenley |
| 2009/0008306 A1 | 1/2009 | Cicchello |
| 2009/0076434 A1 | 3/2009 | Mischelevich |
| 2009/0079578 A1 | 3/2009 | Dvorsky |
| 2009/0080757 A1 | 3/2009 | Roger |
| 2009/0082646 A1 | 3/2009 | Bouton |
| 2009/0082647 A1 | 3/2009 | Busby |
| 2009/0082649 A1 | 3/2009 | Muller |
| 2009/0082653 A1 | 3/2009 | Rohde |
| 2009/0082676 A1 | 3/2009 | Bennison |
| 2009/0095679 A1 | 4/2009 | Demers et al. |
| 2009/0101549 A1* | 4/2009 | Kamen et al. ............ 210/85 |
| 2009/0101552 A1 | 4/2009 | Fulkerson |
| 2009/0101577 A1 | 4/2009 | Fulkerson |
| 2009/0105627 A1 | 4/2009 | Rohde |
| 2009/0112507 A1 | 4/2009 | Edney |
| 2009/0113335 A1 | 4/2009 | Sandoe et al. |
| 2009/0114037 A1 | 5/2009 | Smith |
| 2009/0120864 A1 | 5/2009 | Fulkerson |
| 2009/0124963 A1 | 5/2009 | Hogard |
| 2009/0127193 A1 | 5/2009 | Updyke |
| 2009/0173682 A1 | 7/2009 | Robinson |
| 2009/0282980 A1 | 11/2009 | Gura |
| 2009/0312694 A1 | 12/2009 | Bedingfield et al. |
| 2010/0022936 A1 | 1/2010 | Gura |
| 2010/0094193 A1 | 4/2010 | Gura |
| 2010/0116048 A1 | 5/2010 | Fulkerson |
| 2010/0116740 A1 | 5/2010 | Fulkerson |
| 2010/0179464 A1 | 7/2010 | Smith |
| 2010/0184198 A1 | 7/2010 | Joseph |
| 2010/0209300 A1 | 8/2010 | Dirac |
| 2010/0312161 A1 | 12/2010 | Jonsson |
| 2010/0326916 A1 | 12/2010 | Wrazel |
| 2011/0000830 A1 | 1/2011 | Ikeda |
| 2011/0000832 A1 | 1/2011 | Kelly et al. |
| 2011/0009799 A1 | 1/2011 | Mullick |
| 2011/0028881 A1 | 2/2011 | Basaglia |
| 2011/0028882 A1 | 2/2011 | Basaglia |
| 2011/0041928 A1 | 2/2011 | Volker |
| 2011/0046533 A1 | 2/2011 | Stefani |
| 2011/0054352 A1 | 3/2011 | Ko |
| 2011/0071465 A1 | 3/2011 | Wang |
| 2011/0092907 A1 | 4/2011 | Krogh |
| 2011/0093294 A1 | 4/2011 | Elahi |
| 2011/0098545 A1 | 4/2011 | Ross |
| 2011/0098624 A1 | 4/2011 | McCotter |
| 2011/0098625 A1 | 4/2011 | Masala |
| 2011/0098635 A1 | 4/2011 | Helmore |
| 2011/0105877 A1 | 5/2011 | Wilt |
| 2011/0105981 A1 | 5/2011 | Wagner |
| 2011/0105983 A1 | 5/2011 | Kelly |
| 2011/0105984 A1 | 5/2011 | Patel |
| 2011/0106002 A1 | 5/2011 | Helmore |
| 2011/0106047 A1 | 5/2011 | Burbank |
| 2011/0106466 A1 | 5/2011 | Furmanksi |
| 2011/0107251 A1 | 5/2011 | Guaitoli |
| 2011/0108482 A1 | 5/2011 | Lovell |
| 2011/0125073 A1 | 5/2011 | Rambod |
| 2011/0126714 A1 | 6/2011 | Brugger |
| 2011/0132838 A1 | 6/2011 | Curtis |
| 2011/0132841 A1 | 6/2011 | Rohde |
| 2011/0137224 A1 | 6/2011 | Ibragimov |
| 2011/0137264 A1 | 6/2011 | Chelak |
| 2011/0139704 A1 | 6/2011 | Choi |
| 2011/0140896 A1 | 6/2011 | Menzel |
| 2011/0141116 A1 | 6/2011 | Dalesch |
| 2011/0152739 A1 | 6/2011 | Roncadi |
| 2011/0155657 A1 | 6/2011 | Collins |
| 2011/0160649 A1 | 6/2011 | Pan |
| 2011/0166507 A1 | 7/2011 | Childers |
| 2011/0168614 A1 | 7/2011 | Pouchoulin |
| 2011/0171713 A1 | 7/2011 | Bluchel |
| 2011/0189048 A1 | 8/2011 | Curtis |
| 2011/0208072 A1 | 8/2011 | Pfeiffer |
| 2011/0208106 A1 | 8/2011 | Levin |
| 2011/0213289 A1 | 9/2011 | Toyoda |
| 2011/0218475 A1 | 9/2011 | Brugger |
| 2011/0218487 A1 | 9/2011 | Shang |
| 2011/0226680 A1 | 9/2011 | Jonsson |
| 2011/0230814 A1 | 9/2011 | Kopperschmidt |
| 2011/0237997 A1 | 9/2011 | Beden |
| 2011/0237998 A1 | 9/2011 | Wariar |
| 2011/0240537 A1 | 10/2011 | Ferrarini |
| 2011/0240555 A1 | 10/2011 | Ficheux |
| 2011/0269167 A1 | 11/2011 | Bene |
| 2011/0272352 A1 | 11/2011 | Braig |
| 2011/0275984 A1 | 11/2011 | Biewer |
| 2011/0284464 A1 | 11/2011 | Roncadi |
| 2011/0297593 A1 | 12/2011 | Kelly |
| 2011/0297598 A1 | 12/2011 | Lo |
| 2011/0297599 A1 | 12/2011 | Lo |
| 2011/0300010 A1 | 12/2011 | Jamagin |
| 2011/0300230 A1 | 12/2011 | Peterson |
| 2011/0303588 A1 | 12/2011 | Kelly |
| 2011/0303590 A1 | 12/2011 | Childers |
| 2011/0303598 A1 | 12/2011 | Lo |
| 2011/0309019 A1 | 12/2011 | Ahrens |
| 2011/0315611 A1 | 12/2011 | Fulkerson |
| 2012/0010554 A1 | 1/2012 | Vantard |
| 2012/0018377 A1 | 1/2012 | Tsukamoto |
| 2012/0018378 A1 | 1/2012 | Kelly |
| 2012/0022440 A1 | 1/2012 | Childers |
| 2012/0029324 A1 | 2/2012 | Akonur |
| 2012/0029937 A1 | 2/2012 | Neftel |
| 2012/0031826 A1 | 2/2012 | Childers |
| 2012/0035534 A1 | 2/2012 | Yu |

(56) References Cited

U.S. PATENT DOCUMENTS

| | | |
|---|---|---|
| 2012/0037550 A1 | 2/2012 | Childers |
| 2012/0043279 A1 | 2/2012 | Kelly |
| 2012/0065567 A1 | 3/2012 | Zarate |
| 2012/0075266 A1 | 3/2012 | Shimizu |

FOREIGN PATENT DOCUMENTS

| | | |
|---|---|---|
| WO | 9823353 | 6/1998 |
| WO | 2005089832 | 9/2005 |
| WO | 2005089832 A2 | 9/2005 |
| WO | 2006120415 | 11/2006 |
| WO | 2009045589 | 4/2009 |
| WO | 2009045589 A2 | 4/2009 |
| WO | 2009073567 | 6/2009 |
| WO | 2009091963 | 7/2009 |
| WO | 2010042666 | 4/2010 |
| WO | 2010042667 | 4/2010 |
| WO | 2010062698 | 6/2010 |
| WO | 2010081121 | 7/2010 |
| WO | 2010114932 | 7/2010 |
| WO | 2012108910 | 8/2012 |

OTHER PUBLICATIONS

Reyes et al., "Acid-Base Derangements During Sorbent Regenerative Hemodialysis in Mechanically Ventilated Patients", Critical Care Medicine, vol. 19, No. 4, 1991, 554-559 (col. 2, lines 17-22).
Cobe Renal Care, Inc., "Sorbent Dialysis Primer", Edition 4, Sep. 1993.
Cobe Laboratories, Inc., 'CentrySystem 3 Dialysis Control Unit Operators Manual', Sep. 1988.
Fresenius USA, Inc., "Fresenius 2008H Hemodialysis Machine", Part No. 490005, Revision H, 1994-2001.
Renal Solutions, Inc., 510(K) for the SORB+ and HISORB+ Cartridges, Mar. 31, 2003.
CD Medical, Inc., "Operator's Manual Drake Willock 480 Ultrafiltration Control Single Patient Delivery System", 1988.
Renal Solutions, Inc., 'Dialysate Tubing Set and Dialysate Reservoir Bag for the Allient Sorbent Hemodialysis System', Instructions, 2004.
NxStage Medical, Inc., "NxStage System One User's Guide", Software Version 4.3, Part 1 through Part 6-20, 2006.
NxStage Medical, Inc., "NxStage System One User's Guide", Software Version 4.3, Part 6-20 through Part C-17, 2006.
Manns et al., "The acu-men: A New Device for Continuous Renal Replacement Therapy in Acute Renal Failure", Kidney International, vol. 54 (1998), 268-274.
REDY 2000 Operator's Manual (1991) (Sorbent cartridge-based hemodialysis system).
REDY 2000 Service Manual (1989) (Sorbent cartridge-based hemodialysis system).
Seratron Dialysis Control System Operations Manual (cumulative 1980).
Ward et al., 'Sorbent Dialysis Regenerated Dialysis Delivery Systems', Peritoneal Dialysis Bulletin, Chapter 8, 3(2): S41-S48 (Apr.-Jun. 1983).
Anthony J. Wing et al., 'Dialysate Regeneration', Replacement of Renal Function by Dialysis, Chapter 17, 323-340 (William Drukker et al., eds., Martinus Nijhoff Publishers, 2nd ed., 1983).
Fresenius AG, 'Acumen Acute Dialysis Machine Operating Instructions', Version 1.0, May 1996.

Renal Solutions, Special 510(k) Device Modification, Allient Sorbent Hemodialysis System, Mar. 15, 2007.
International Search Report for PCT/US09/59906, Xcorporeal, Inc., dated May 8, 2012.
International Search Report for PCT/US09/62840, Xcorporeal, Inc. dated Feb. 10, 2012.
International Search Report for PCT/US11/53184, Xcorporeal, Inc., dated Mar. 2, 2012.
International Search Report for PCT/US09/31228, Xcorporeal, Inc., dated Jun. 19, 2009.
International Search Report for PCT/US09/59907, Xcorporeal, Inc., dated Apr. 13, 2010.
International Search Report for PCT/US10/29500, Xcorporeal, Inc., dated Jul. 2, 2010.
Examination Report for PCT/US09/59906, New Zealand Intellectual Property Office, dated May 15, 2012.
Examination Report for PCT/US08/85062, Mexican Patent Office, dated Mar. 11, 2013.
Search report for PCT/US10/20698, dated Jul. 15, 2010, XCorporeal, Inc.
Renal Solutions, Portions of the Allient Sorbent Hemodialysis System, Operator Manual Model 1500, 2008, Chapter 3, 3-31 to 3-70.
Renal Solutions, Portions of the Allient Sorbent Hemodialysis System, Operator Manual Model 1500, 2008, Chapters 1 to 2.
Renal Solutions, Portions of the Allient Sorbent Hemodialysis System, Operator Manual Model 1500, 2008, Chapter 3, 3-2 to 3-30.
Renal Solutions, Portions of the Allient Sorbent Hemodialysis System, Operator Manual, 2008, Chapters 1 to 2.
Renal Solutions, Portions of the Allient Sorbent Hemodialysis System, Operator Manual, 2008, Chapter 3.
Renal Solutions, Portions of the Allient Sorbent Hemodialysis System, Operator Manual, 2008, Chapter 4, 4-1 to 4-33.
Renal Solutions, Portions of the Allient Sorbent Hemodialysis System, Operator Manual, 2008, Chapter 4, 4-34 to 4-69.
Renal Solutions, Portions of the Allient Sorbent Hemodialysis System, Operator Manual, 2008, Chapter 5.
International Search Report for PCT/US10/20698, Xcorporeal, Inc., dated Jun. 16, 2010.
Renal Solutions, Inc., Portions of 510(k) Allient Sorbent Hemodialysis System (Sections A-I), Dec. 17, 2004.
Renal Solutions, Inc., Portions of 510(k) Allient Sorbent Hemodialysis System (Allient Main Controller Software Architecture Overview), Renal Solutions, Inc., Dec. 17, 2004.
Renal Solutions, Inc., Portions of 510(k) Allient Sorbent Hemodialysis System (Sections M.3 and M.4), Renal Solutions, Inc., Dec. 17, 2004.
Renal Solutions, Portions of the Allient Sorbent Hemodialysis System, Home User Manual, 2006, Chapters 1-3.
Renal Solutions, Portions of the Allient Sorbent Hemodialysis System, Home User Manual, 2006, Chapters 4.
Renal Solutions, Portions of the Allient Sorbent Hemodialysis System, Home User Manual, 2006, Chapters 5 to end.
International Preliminary Report on Patentability for PCT/US2009/059907, dated Apr. 15, 2010, Fresenius Medical Care Holdings, Inc.
International Search Report for PCT/US2009/059907, dated Apr. 15, 2010, Fresenius Medical Care Holdings, Inc.
Timby et al., Introductory Medical-Surgical Nursing, Lippincott Williams Wilkins, Ninth Edition, Chapter 28, p. 433.
International Search Report PCT/US08/85062, dated Mar. 20, 2009, XCorporeal, Inc.
International Search Report PCT/US10/29500, dated Jul. 20, 2010, XCorporeal, Inc.

\* cited by examiner

MODULAR, PORTABLE DIALYSIS SYSTEM

CROSS-REFERENCE

The present invention relies on U.S. Patent Provisional No. 61/109,834, filed on Oct. 30, 2008, for priority. The present invention is also related to U.S. patent application Ser. Nos. 12/575,450, filed on Oct. 7, 2009, Ser. No. 12/575,449, filed on Oct. 7, 2009, Ser. No. 12/355,102, filed on Jan. 16, 2009, Ser. No. 12/355,128, filed on Jan. 16, 2009, Ser. No. 12/351,969, filed on Jan. 12, 2009, Ser. No. 12/324,924, filed on Nov. 28, 2008, Ser. No. 12/210,080, filed on Sep. 12, 2008, Ser. No. 12/238,055, filed on Sep. 25, 2008, Ser. No. 12/237,914, filed on Sep. 25, 2008, Ser. No. 12/249,090, filed on Oct. 10, 2008, and Ser. No. 12/245,397, filed on Oct. 3, 2008. All of the aforementioned applications are herein incorporated by reference.

FIELD OF THE INVENTION

The present invention is directed to a dialysis system with improved structural and functional features. In particular, the dialysis system of the present invention is directed to a portable dialysis system with improved modularity, ease of use, and safety features.

BACKGROUND OF THE INVENTION

Hemodialysis is used for removing toxic wastes from the human body in cases of renal failure. The patient's blood is temporarily brought outside of the body via tubes and passed through at least one semi-permeable membrane, which may be a group of hollow fibers, in a dialyzer. The semi-permeable membrane separates the blood from a dialysate solution. Impurities from the blood pass through the membrane and into the dialysate solutions, primarily by osmotic pressure. The cleansed blood is then returned to the body.

Standard dialysis treatment, using an installed apparatus in hospitals, comprises two phases, namely, (a) dialysis, in which toxic substances and scoriae (normally small molecules) pass through the semi-permeable membrane from the blood to the dialysis liquid, and (b) ultrafiltration, in which a pressure difference between the blood circuit and the dialysate circuit, more precisely a reduced pressure in the latter circuit, causes the blood content of water to be reduced by a predetermined amount.

Dialysis procedures using standard equipment tend to be cumbersome as well as costly, besides requiring the patient to be bound to a dialysis center for long durations. Portable dialysis systems have been developed. U.S. Pat. No. 4,083,777 discloses a hemodialysis system with dialyzer means through which waste impurity-containing blood and a dialysate solution are passed in indirect mass transfer dialyzing relationship for transfer of the waste impurities from the blood to the dialysate solution. The apparatus includes means for transferring waste impurity-containing blood from a patient to said dialyzer means including a flexible resilient tubing pumping section through which blood is pumped and means for returning waste impurity depleted blood to the patient forming a blood flow circuit. Peristaltic pump means are provided with a rotatable pump head assembly including a base member positioned for rotation about a fixed axis with a plurality of circumferentially spaced apart rollers mounted thereon for independent rotation about respective axes parallel to the base member fixed axis.

U.S. Pat. No. 4,443,333 discloses a portable system for dialyzing blood wherein blood passes through an exchange station with the blood contacting one side of a semipermeable membrane and dialysate contacting the other side of the semipermeable membrane, the system comprising elastic tube means adapted to be connected to a blood source and to return blood thereto for conducting blood past a plurality of stations, a blood clot detector and an air bubble detector in communication with said blood tube means, elastic tube means adapted to be connected to a source of dialysate for conducting dialysate past a plurality of stations, means for measuring and regulating dialysate flow, pressure, temperature and conductivity, means for maintaining the dialysate at a lower pressure than the blood during passage through the exchange station, a single motor means having the output shaft thereof connected to at least two peristaltic pumps one for transporting blood in the elastic blood means and the other for transporting dialysate in the elastic dialysate tube means, mechanism associated with the motor means and the peristaltic pumps for maintaining the dialysate flow at about three times the blood flow, each of the peristaltic pumps having an inner arcuate surface, the blood pump having at least one roller associated with the inner arcuate bearing surface to trap the blood tube means therebetween, the dialysate pump having a single roller associated with said inner arcuate bearing surface to trap said dialysate tube means therebetween, actuation of the peristaltic blood pump causing smooth laminar flow of blood in the blood tube means due to the roller, actuation of the peristaltic dialysate pump causing dialysate flow due to a vacuum generated by the single roller resulting in the deformation and return of the elastic dialysate tube means, and control mechanism operatively connected to the blood leak detector and the air bubble detector and to the motor means and to the dialysate flow, pressure, temperature and conductivity measuring means for selectively stopping the dialysate roller thereby halting movement of dialysate through the dialysate tube means and through the exchange station in response to pressure or temperature or conductivity measurements outside of a preselected range while maintaining blood flow and for simultaneously stopping all the rollers in response to a signal from either the blood leak detector or the air bubble detector to shut down the entire system and halt pumping.

U.S. Pat. No. 6,168,578 discloses a portable kidney dialysis system that includes a belt with a drain bag mounted thereon. A pump is also mounted on the belt and coupled between a user and the drain bag. The pump is adapted to pump fluid from the user to the drain bag upon the receipt of a drain signal. Further provided is a pressure switch for detecting when the drain bag is full. A control mechanism serves for transmitting the drain signal to the pump only when the means fails to detect that the drain bag is full. A portable dialysis system called System One made by NxStage is another example of a conventional portable hemodialysis system.

The aforementioned portable dialysis systems suffer from certain disadvantages. First, they are not sufficiently modular, thereby preventing the easy setup, movement, shipping, and maintenance of the systems. Second, the systems are not simplified enough for reliable, accurate use by a patient. The systems' interfaces and methods of using disposable components are subject to misuse and/or errors in usage by patients. For a portable dialysis system to be truly effective, it should be easily and readily used by individuals who are not health-care professionals, with disposable input and data input sufficiently constrained to prevent inaccurate use.

It is therefore desirable to have a portable dialysis system that has a structural design configured to optimize the modularity of the system, thereby enabling the easy setup, movement, shipping, and maintenance of the system. It is further desirable to have system interfaces, through which patients input data or deploy disposable components, configured to prevent errors in usage and sufficiently constrained to prevent inaccurate use.

SUMMARY OF THE INVENTION

The present invention is directed toward a modular dialysis system comprising a controller unit having a first external housing with a front side, a back side, a left side, a right side, a top side and a bottom side, wherein said front side comprises a door configured to provide access to an internal volume within said controller unit; a reservoir unit having a second external housing with a front side, a back side, a left side, a right side, a top side and a bottom side, wherein said front side comprises a door configured to provide access to an internal volume within said reservoir unit; wherein said bottom side of the first external housing is adapted to securely and removably attach to said top side of the second external housing and wherein, when said first external housing is securely and removably attached to said second external housing, the controller unit is automatically placed in electrical communication with said reservoir unit.

Optionally, the bottom side of the first external housing comprises an electrical contact pad and the top side of the second external housing comprises a plurality of electrical pins. Optionally, the bottom side of the first external housing comprises a plurality of electrical pins and the top side of the second external housing comprises an electrical contact pad. The controller unit is automatically placed in electrical communication with said reservoir unit when the contact pad is aligned and placed in electrical communication with the plurality of push-pins.

Optionally, when said first external housing is securely and removably attached to said second external housing, the controller unit is automatically placed in data communication with said reservoir unit. The bottom side of the first external housing comprises a first infrared communication port having at least one LED transmitter and at least one LED receiver and the top side of the second external housing comprises a second infrared communication port having at least one LED transmitter and at least one LED receiver. The controller unit is automatically placed in data communication with said reservoir unit when the first infrared communication port is aligned and placed in data communication with the second infrared communication port.

Optionally, the internal volume within said controller unit houses a manifold, a hook, and a guard encircling the manifold. The door configured to provide access to the internal volume within said controller unit has an internal surface and said internal surface comprises a plurality of pump shoes, a latch, and casing with sides that protrude into said internal volume when said door is closed. When the door is closed, said latch mechanically engages said hook. The modular dialysis system further comprises a controller configured to actuate a motor to apply a motive force to said hook and said application of motive force causes said door to be closed with a force in a range of 90 to 110 lbs. The modular dialysis system further comprises a mechanical release button having a first state and a second state, wherein, in said first state, the button is capable of mechanically engaging said hook and wherein, in said second state, the button is not capable of mechanically engaging said hook.

In another embodiment, the present invention is directed to a modular dialysis system comprising a controller unit having a first external housing with a front side, a back side, a left side, a right side, a top side and a bottom side, wherein said front side comprises a door configured to provide access to an internal volume within said controller unit; a reservoir unit having a second external housing with a front side, a back side, a left side, a right side, a top side and a bottom side, wherein said front side comprises a door configured to provide access to an internal volume within said reservoir unit, wherein said top side has an angled surface with a plurality of channels in fluid communication with at least one leak detector; and wherein said bottom side of the first external housing is adapted to securely and removably attach to said top side of the second external housing.

Optionally, the bottom side of the first external housing comprises an electrical contact pad and the top side of the second external housing comprises a plurality of electrical pins. The controller unit is automatically placed in electrical communication with said reservoir unit when the contact pad is aligned and placed in electrical communication with the plurality of push-pins. The bottom side of the first external housing comprises a first infrared communication port having at least one LED transmitter and at least one LED receiver and the top side of the second external housing comprises a second infrared communication port having at least one LED transmitter and at least one LED receiver. The controller unit is automatically placed in data communication with said reservoir unit when the first infrared communication port is aligned and placed in data communication with the second infrared communication port.

Optionally, the internal volume within said controller unit houses a hook and the door configured to provide access to the internal volume within said controller unit has an internal surface that comprises a latch. The modular dialysis system further comprises a controller configured to actuate a motor to apply a motive force to said hook in response to a user input and said application of motive force causes said door to be closed with a force in a range of 90 to 110 lbs. The modular dialysis system further comprises a mechanical release button having a first state and a second state, wherein, in said first state, the button is capable of mechanically engaging said hook and wherein, in said second state, the button is not capable of mechanically engaging said hook.

These and other embodiments will be described in more detail in the Detailed Description section in relation to the Drawings.

BRIEF DESCRIPTION OF THE DRAWINGS

Embodiments of the present invention are described in greater detail with respect to the following drawings.

DETAILED DESCRIPTION OF THE INVENTION

Figure 1:
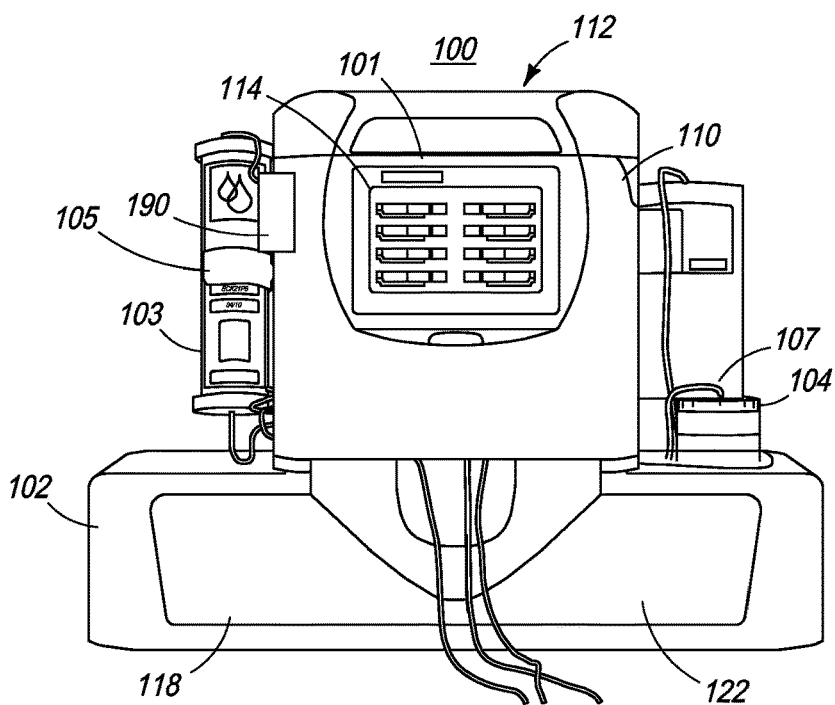
FIG. 1 is a front view of the dialysis system of the present invention.

While the present invention may be embodied in many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

"Duration" and variations thereof refer to the time course of a prescribed treatment, from initiation to conclusion, whether the treatment is concluded because the condition is resolved or the treatment is suspended for any reason. Over the duration of treatment, a plurality of treatment periods may be prescribed during which one or more prescribed stimuli are administered to the subject.

"Period" refers to the time over which a "dose" of stimulation is administered to a subject as part of the prescribe treatment plan.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," "one or more," and "at least one" are used interchangeably and mean one or more than one.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

Figure 2:
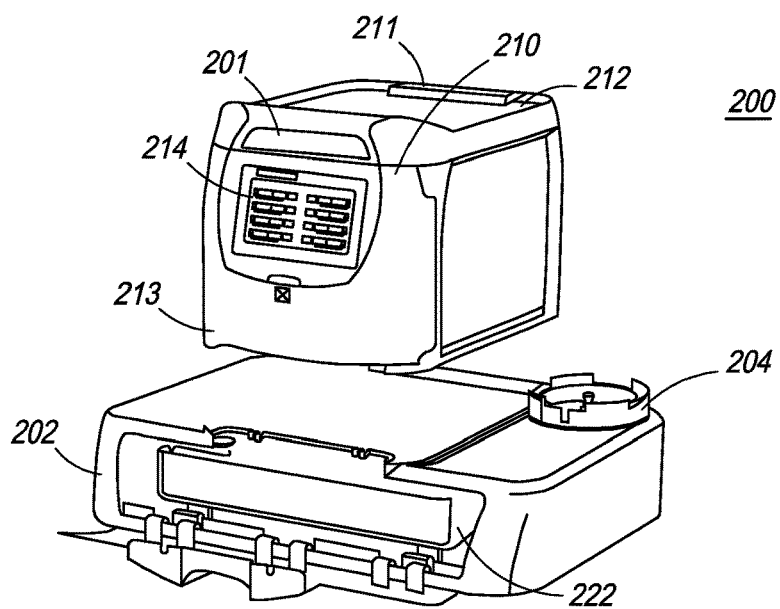
FIG. 2 is view of the dialysis system showing the modularity of the system.
Figure 3:
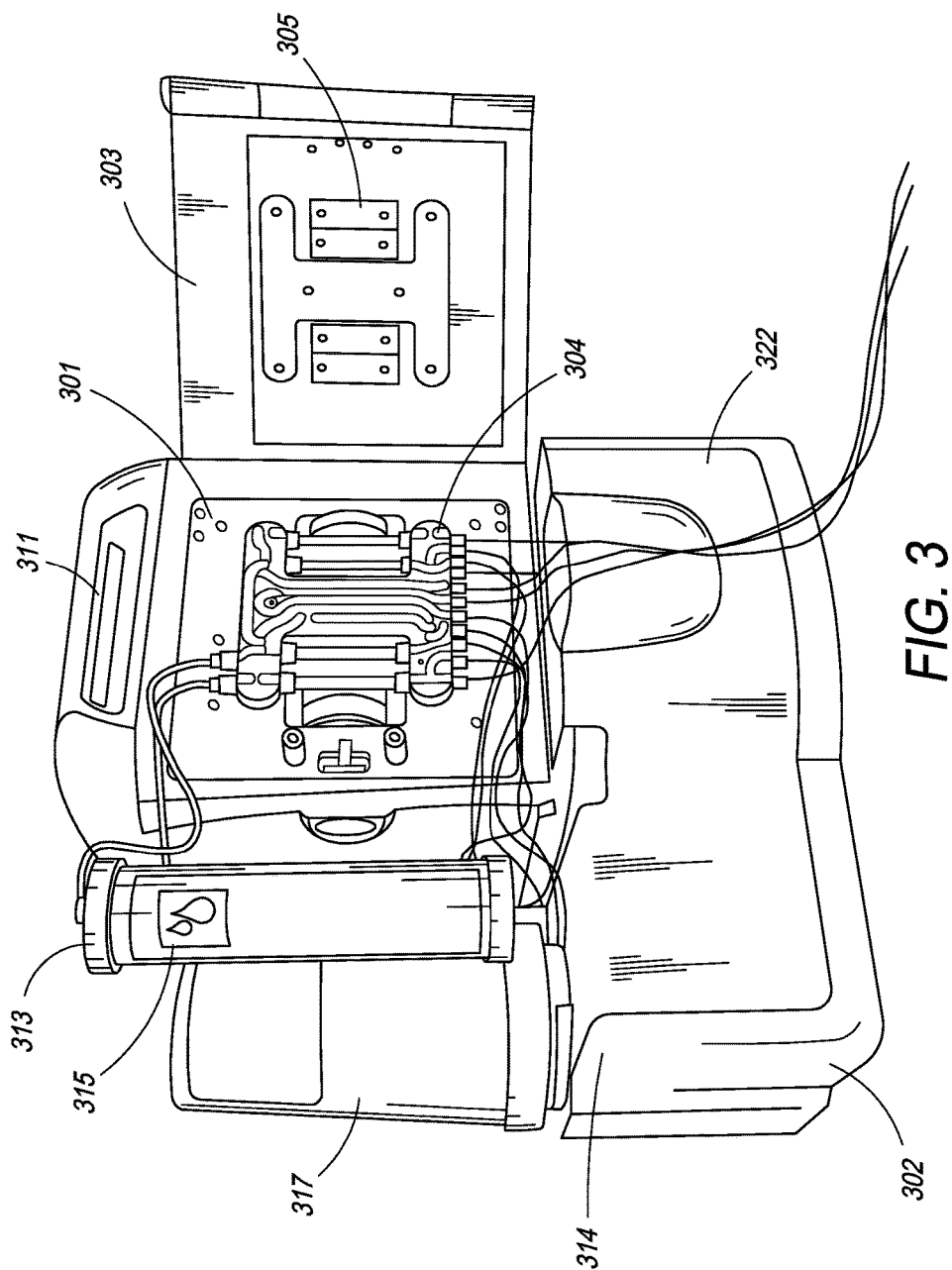
FIG. 3 is a view of the back of the dialysis system, with the door open.

The present invention is directed toward a dialysis unit that is modular and portable, with improved functionality. Referring to FIGS. 1 and 2, in one embodiment, the dialysis system 100, 200 comprises a top unit 101, 201 that is detachably affixed to a base 202 that comprises a reservoir 122, 222 for fluid storage. The top unit 101, 201, also referred to as the main unit or controller unit, comprises a graphical user interface 114, 214, pumping unit, and a door 110, 210 with a power lock and mechanical backup mechanism, as further discussed below. To a first side of the top unit 101, 201 is a clasp 105 used to detachably affix a dialyzer 103. To a second side of the top unit 101, 201 is a sorbent cartridge locking base 104, 204 used to detachably affix a sorbent cartridge 107. It should be appreciated that the clasp 105, hemofilter 103, sorbent cartridge locking base 104 and sorbent cartridge 107 can be positioned on the same side of the top unit 101, as shown in FIG. 3. In either case, the bottom unit has a sufficiently larger area relative to the top unit such that shelves are formed on either side of the top unit to hold the sorbent cartridge, to hold an infusate jar, to capture any spillage, and/or to channel any leaks into a leak detector.

Between the dialyzer 103 and door 110 are anti-coagulant pumps in the form of syringe pumps 190. Optionally, the top unit 101 can comprise a bottle holder 190 that has a spiked base to receive a bottle, top-down, within the bottle holder housing. Infusion lines are connected to the inlet of the blood pump, outlet of the blood pump, or outlet of the dialyzer (blood side). The infusion lines could also 'thread' through air bubble detectors to sense if/when the anticoagulant is emptied or blocked.

The dialysis system of the present invention achieves functional and operational parameters that represent a substantial improvement over the prior art. The top unit is in the range of approximately 20-40 pounds, and more particularly 30 pounds, and the bottom unit is in the range of approximately 15-30 pounds, and more particularly 22 pounds, thereby weighing less than prior art systems. The top unit is in the range of approximately 1 to 4 cubic feet, and more particularly 2.3 cubic feet, and the bottom unit is in the range of approximately 1 to 4 cubic feet, and more particularly 2.8 cubic feet, thereby having a smaller volume than prior art systems.

Figure 17A:
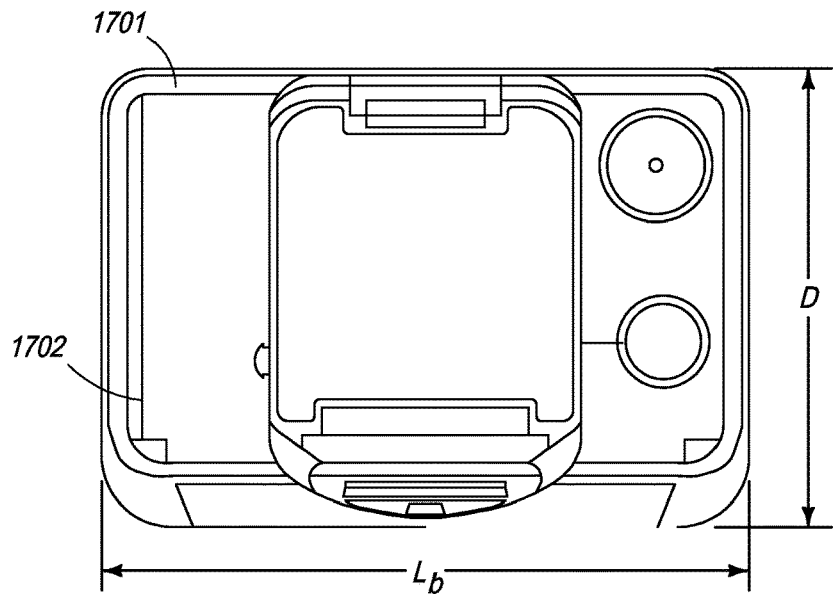
FIG. 17a is a top view of one embodiment of the portable dialysis system with exemplary dimensions denoted.
Figure 17B:
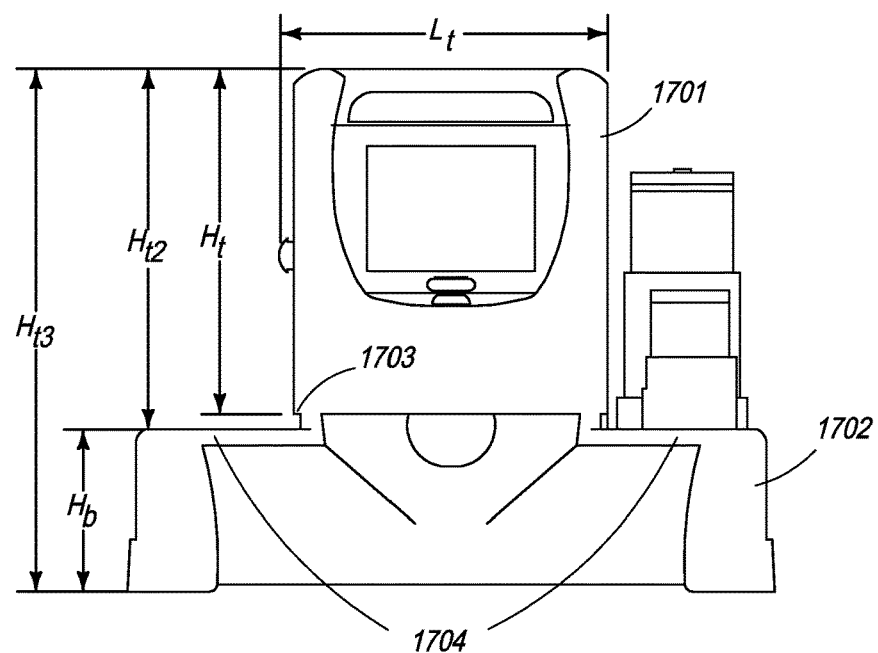
FIG. 17b is a front view of one embodiment of the portable dialysis system with exemplary dimensions denoted.

In one embodiment, referring to FIG. 17, the top unit 1701, which comprises the user interface and controller, has the same depth, but a different length and height than the base unit 1702, which comprises a reservoir integrated with a scale. In this exemplary embodiment, both the top unit 1701 and bottom unit 1702 have a depth D in the range of 10 to 30 inches, more preferably approximately 19 inches. In this exemplary embodiment, the top unit 1701 has a length Lt in the range of 6 to 20 inches, more preferably approximately 14 inches, while the bottom unit has a length Lb in the range of 14 to 40 inches, more preferably 27 inches. In this exemplary embodiment, the top unit 1701 has a height Ht in the range of 7 to 21 inches, more preferably approximately 14.5 inches, while the bottom unit has a height Hb in the range of 3 to 11 inches, more preferably 7 inches.

The base unit 1702 may further be defined by two shoulders 1704, each extending outward, along the length of the base unit 1702, from the sides of a centrally positioned top unit 1701. The top unit is preferably positioned in the center of the base unit 1702, as measured by length Lb. Accordingly, the shoulder 1704 can be defined has having a length in the range of 4 inches to 10 inches, more preferably approximately 7 inches. Extending upward from the surface of the base unit 1702, where shoulders 1704 physically meet top unit 1701, is a lip 1703 that defines a surface upon which top unit 1701 is aligned and placed. The lip 1703 is contiguous around the base of the top unit 1701, having the same length and depth as the top unit 1701, with a height defined as the difference between Ht2 and Ht. In one embodiment, the lip height is in the range of 0.1 to 3.5 inches, more preferably 0.6 inches. The overall height of the system, Ht3, is in the range of 10 to 35 inches, more preferably 22 inches.

The external housing structures defining the top unit 1701 and base unit 1702 may be characterized as rectangular parallelpipeds, cuboids, or boxes, each with four sides, a top, and a bottom. In an exemplary embodiment, for both the top unit 1701 and base unit 1702, two of the four sides, each having an exterior and interior surface, have the same height, length, and depth, while the top and bottom structures, each having an exterior and interior surface, have the same height, length, and depth.

It should be appreciated that the system configuration shown in FIGS. 1, 2, 17a, and 17b is exemplary and not limiting. For example, shown in FIG. 3, the top unit 301 may be positioned on one side of the base unit 302 (creating an asymmetric base), as opposed to being centrally positioned on top of the base unit 302 relative to the overall length of the base unit 302 (creating a symmetric base). While placement of the top unit 301 to one side of the base unit 302 has the advantage of placing all tubing connections and consumables on the same side of the system, sorbent cartridge 317 and dialyzer 313 are unnecessarily crowded together, making the machine more difficult to use.

The dialysis system uses less water than prior art systems. Conventional systems use approximately 120 liters per treatment. In one embodiment, the present systems uses between 3 and 8 liters, and more particularly between 5 and 6 liters. Furthermore, the system does not require a home drain, supply connection, or separate outlet to address excess water.

Additionally, in one embodiment, the present invention uses a multi-pass sorbent system, as disclosed in XCORP212 and incorporated herein by reference. Accordingly, the system does not require a separate purified water input with a reverse osmosis system and, instead, can use regular tap water that is then purified using the sorbent system.

Furthermore, the system design is more compact, with low power requirements (only 300 at peak and 50 to 100 W during operation), no separate fluid bags required for priming or travel, and integrated pumps. The device operates using a blood flow range of 20-600 Qb (ml/min), a dialysate flow of 50-500 Qd (ml/min). The volumetric accuracy is also precise at less than +/−30 ml/hr.

As demonstrated in FIG. 2, the dialysis system is modular. In one embodiment, the top unit 201 can be physically separated from the bottom unit 202. The top unit 201 contains the primary electronics of the system, including the graphical user interface, controllers, and pumps, integrally formed into a self-contained housing. The larger, bulkier bottom unit 202 contains the reservoir 222. Separation of the system electronics from the reservoir allows the portable dialysis system to be separated into multiple units for installation, service, and travel, with each subunit being easily handled, packaged and carried. The design specifically sizes components for shipping via UPS or other door to door carriers. It further provides flexibility in product growth. For example, if improvements are made to the controller unit or, separately, to the reservoir (such as reducing fluid volume or a change in volume scale measurement), an existing customer need only upgrade one of the two component parts, not both. Similarly, if only one of the two components breaks (e.g. the pump burns out), a customer need only send in one for repair or purchase one of the two components.

To enable the above described modularity, embodiments of the present invention employ a latching mechanism that, in a first configuration, securely attaches the bottom unit 202 to the top unit 201 and can be manipulated to removably detach the bottom unit 202 from the top unit 201. Even though the two systems could be simply stacked atop each other, without a latch, the presence and use of a latch reduces the likelihood of an accidental disconnection. Furthermore, when latched together the device is easier to move. The latch mechanism preferably uses no tools and is simply achieved using a male/female mating connections present on the top component and bottom component. Further preferably, the latch mechanism is designed to ensure solid alignment between the top and bottom components, thereby enabling the use of an electronic components (such as exposed electronic connectors on the bottom of the top unit and top of the bottom unit as further described below) which, when the units are properly aligned, automatically come into contact and complete a power circuit. This permits the use of a single power supply and simple connection/disconnection.

Figure 14:
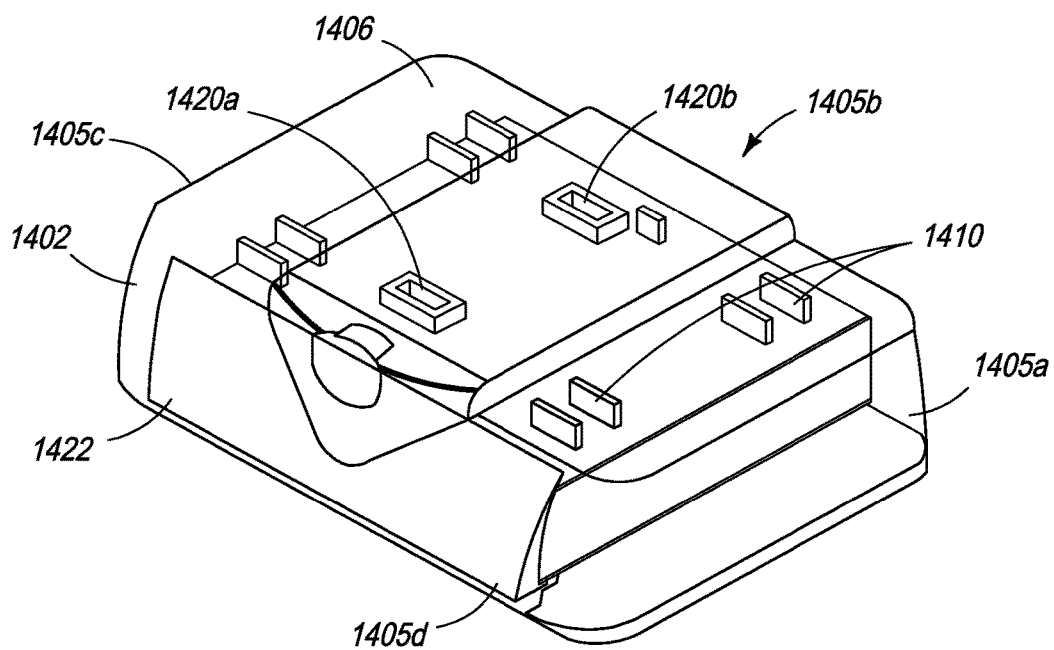
FIG. 14 is a first side perspective view of one embodiment of a base unit of the portable dialysis system with a matching latching mechanism.

Referring to FIG. 14, the bottom unit 1402 has four sides 1405a, 1405b, 1405c, 1405d, a base, a top surface 1406, and a reservoir 1422 accessible via first side 1405*d*. The bottom unit 1402 further comprises a plurality of latch mating structures 1420 on its top surface 1406. In one embodiment, the present invention comprises two latch mating structures 1420*a*, 1420*b* that, relative to the length of the bottom unit 1402, are centrally positioned to ensure even weight distribution. The first latch mating structure 1420*a* is preferably positioned a distance equal to one third of the width of the bottom unit 1402, as measured from side 1405*d*. The second latch mating structure 1420*b* is preferably positioned a distance equal to one third of the width of the bottom unit 1402, as measured from side 1405*b*.

Figure 15:
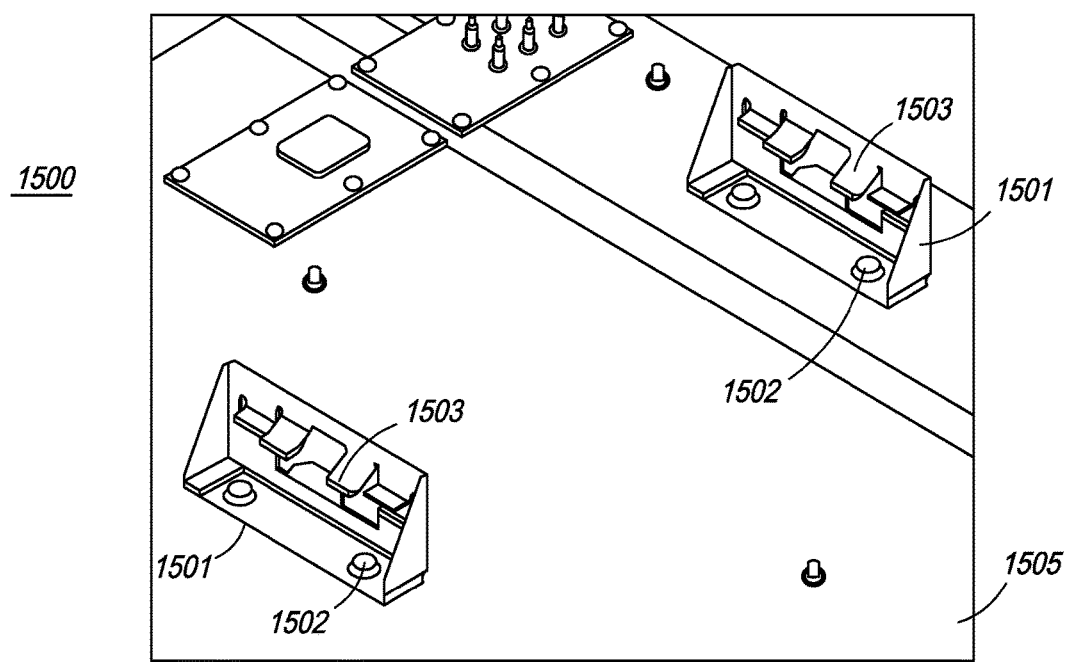
FIG. 15 is a second side perspective view of one embodiment of a base unit of the portable dialysis system with a matching latching mechanism.

The latching mechanisms, as shown in FIG. 15, comprise a metal frame 1501 that is securely fastened using, for example, a bolt, screw, or other fastener 1502, to the top surface of the bottom unit 1505. The frame 1501 supports a protusion or elongated member 1503 that can flexibly insert into, and be removed from, a corresponding latch.

To securely and removably attach the bottom unit to the top unit, the top unit comprises complementary mechanical sliding latches, which are securely attached to the base of the top unit. In one embodiment, the base of the top unit comprises a first latch that is preferably positioned in the center of top unit, relative to the length of the top unit, and a distance equal to one third of the width of the top unit, as measured from a first side. The base also comprises a second latch that is preferably positioned in the center of top unit, relative to the length of the top unit, and a distance equal to one third of the width of the top unit, as measured from a second side, which is opposite and parallel to the first side.

Figure 13:
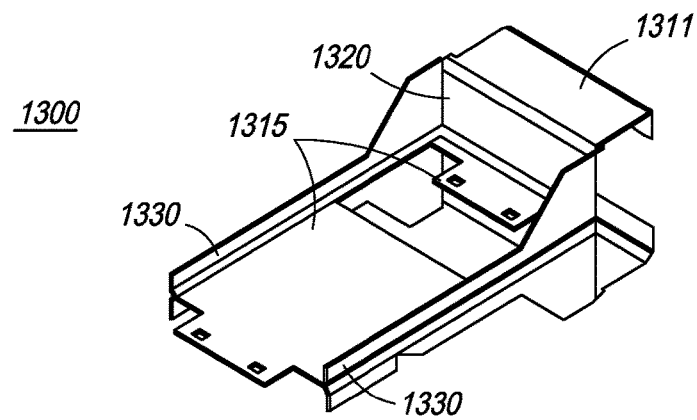
FIG. 13 is a side perspective view of one embodiment of a latch attached to an upper unit of the portable dialysis system.

As shown in FIG. 13, the top unit comprises a latch 1300 with a sliding metal flat base 1315. Rails 1330 are slidably engaged with the bottom surface of the top unit, which has mating members to hold the rails 1330 in place. The latch 1300 has two latching tabs 1315 which are adapted to slide into, and out of, mating structures physically attached to the top surface of the base unit 1406.

Latches 1300, attached to the top unit, mate with latch mating structures 1420*a*, 1420*b* on the top surface of the bottom unit 1406. In operation, when the sliding latch 1300 is in a first position, the top unit will not effectively fit on top of, or align with, the base unit because the sliding latch 1300 will not properly physically mate with latch mating structures 1420*a*, 1420*b*. To prepare the top unit for secure placement on to the top surface of the base unit 1406, the sliding latches are moved within the member holding structure positioned on the bottom of the top unit and placed into a second position.

Figure 18A:
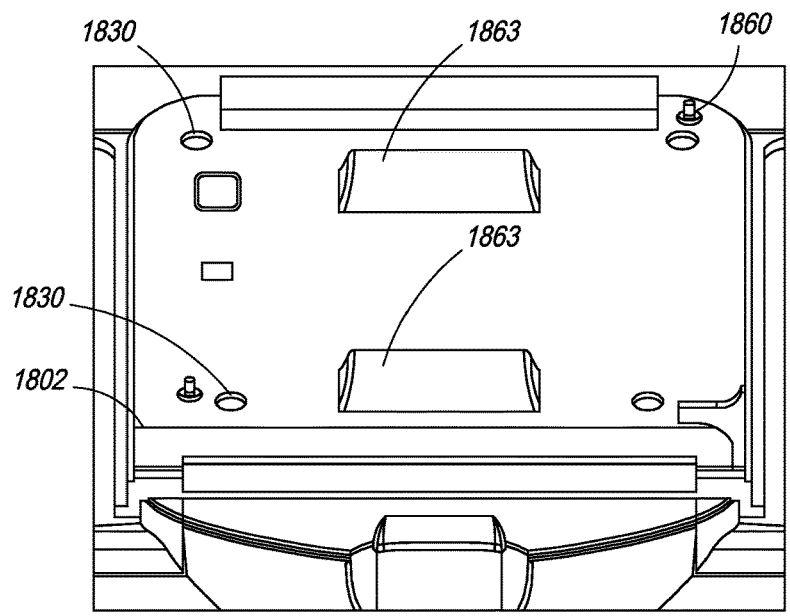
FIG. 18a is a view of one embodiment of the base unit with receiving cavities and alignment pins.
Figure 18B:
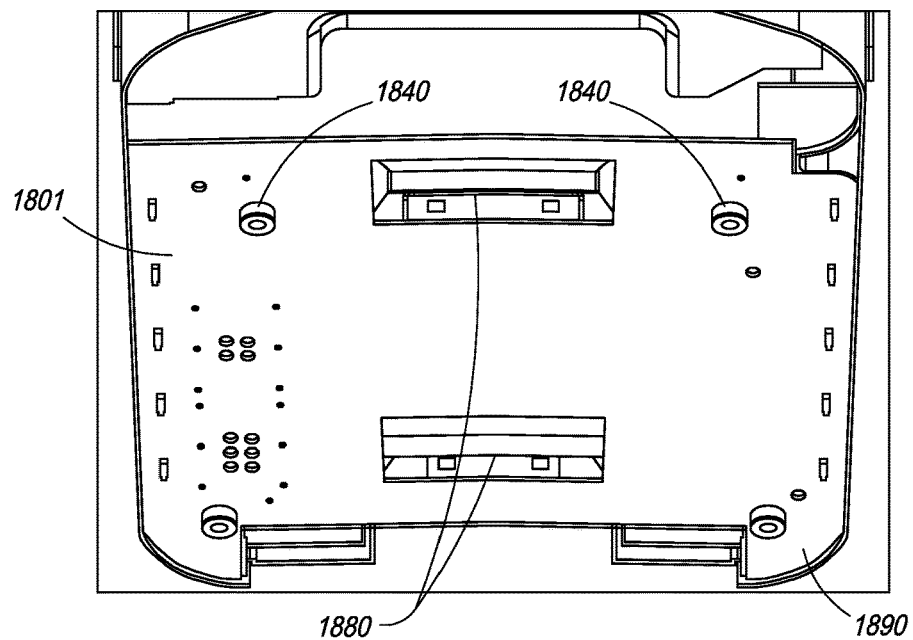
FIG. 18b is a view of one embodiment of the top unit with footing pads.

In the second position, the handle of the latch 1311 will protrude, thereby moving the tabs 1315 away from the latch mating structures 1420*a*, 1420*b* and allowing the top unit to sit correctly on the base unit. Referring to FIGS. 18*a* and 18*b*, the top unit 1801, which has sliding latches 1880, is aligned to the bottom unit 1802 by four small rubber feet, or footing pads, 1840 on the bottom of the top unit 1801, which are configured or adapted to snugly and securely fit into four cavities or pockets 1830 located proximate to each corner on the top of the bottom unit 1802. Additionally, the top unit 1801 can be accurately aligned to the bottom unit 1802 using alignment pins 1860, or protusions, on the top surface of the base unit 1802, which are configured or adapted to securely and snugly fit into corresponding cavities 1890 on the bottom surface of the top unit 1801. The bottom unit also has latch mating structures 1863, as described above.

Aligning the rubber footings 1840 into the cavities 1830 and the pins 1860 into the cavities 1880 ensures that latches 1880 on the top unit 1801 can be readily aligned and latched to the latch matching structures 1863 without excessive trial and error. Once aligned, the latch 1880 is mated with the latch mating structures 1863 by sliding the latches 1880 into the latch mating structures 1863, thereby creating a tight fit between the two units. Referring back to FIGS. 13 and 14, to unlatch, latch handles 1311 are pulled or otherwise manipulated, thereby releasing tabs 1315 from the base unit slots 1420*a*, 1420*b*, and allowing the top, upper unit to be lifted from the bottom, lower unit.

Furthermore, to enable the above described modularity, embodiments of the present invention also employ an electrical and communication connection mechanism that, in a first configuration, securely establishes electrical communication and/or data communication connection between the bottom unit and the top unit and, in a second configuration, terminates an electrical communication and/or data communication connection between the bottom unit to the top unit.

Figure 16:
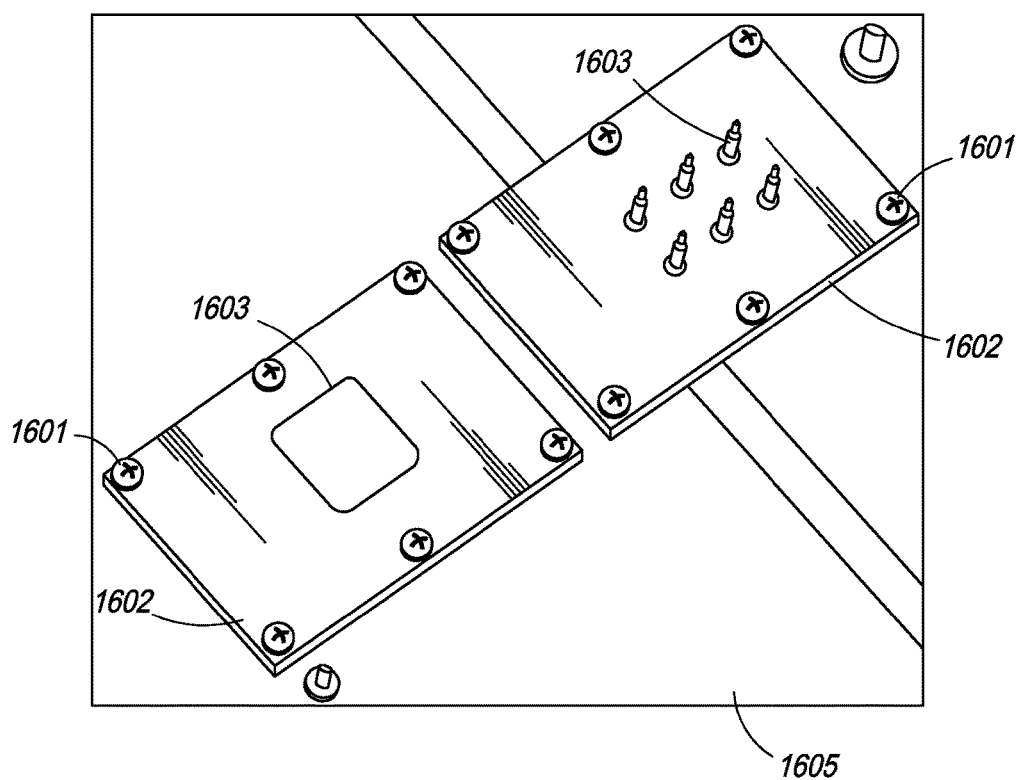
FIG. 16 is a top view of electrical and communication connections implemented in one embodiment of the portable dialysis system.

Referring to FIG. 16, the electrical connections between the top and bottom units are created when the top unit is placed on the bottom unit. These connections are made through a non-contact infrared communications port 1603 and a push-pin power port 1603, which are integrally formed into plates 1602 and securely attached using fasteners 1601 to the top surface of the bottom unit 1605. It should be appreciated that the bottom surface of the top unit would then comprise, in proper alignment with the push-pins, an electrical contact pad. It should further be appreciated that the location of the push-pins and contact pads can be reversed, thereby placing the push-pins on the bottom surface of the top unit and the contact pad on the top surface of the bottom unit.

In one embodiment, a high current power connection is created by placing six spring loaded pins into electrical contact with contact pads, which are integrated into the bottom surface of the top unit. Three pins are for +24 volt DC current and three pins are for ground. In one embodiment, the pins or probes have the following characteristics: a) minimum center of 0.175 inches, b) current rating of 15 amps (continuous), c) spring force in the range of 6.2 oz to 9.0 oz at 0.06 inches to 0.067 inches of travel, d) typical resistance of less than 10 mΩ, e) maximum travel in the range of 0.09 to 0.1 inches, f) working travel in the range of 0.06 to 0.067 inches, g) barrel made of nickel/silver and gold plated, h) stainless steel spring (optionally gold plated), i) plunger made of full-hard beryllium copper and gold plated, and j) optionally a stainless steel bias ball. The spring force of the pins assists in preventing breakage by absorbing bending or other contortions. It should be appreciated that the term electrical pins represents any protusion capable of transmitting electrical power and electrical contact paid represents any surface capable of receiving an electrical pin.

The non-contact infrared communication port 1603 employs two LED transmitters and two LED receivers which align to, and communicate with, two LED transmitters and two LED receivers on the bottom surface of the top unit. The distance between the transmit and receive ports is less than 0.3 inches. On both the top surface of the bottom unit and bottom surface of the top unit, the four LED units are divided into two pairs, a control pair (comprising one transmitter and one receiver) and one safety pair (comprising one transmitter and one receiver). These ports are placed in data communication when the top and bottom units are properly aligned. In one embodiment, the LED transmitters are high speed infrared emitting diodes, 870 nm, made of GaAlAs double hetero technology. The LED transmitters are high speed diodes having the following characteristics: a) extra high radiant power, b) low forward voltage, c) suitable for high pulse current operation, d) angle of half intensity of approximately 17 degrees, e) peak wavelength of approximately 870 nm, f) reverse voltage of approximately 5V, g) forward current of approximately 100 mA, h) a peak forward current of approximately 200 mA, i) surge forward current of approximately 0.8 A, j) power dissipation of approximately 190 mW) junction temperature of approximately 100 degrees Celsius, and l) an operating temperature range of −40 to 85 degrees Celsius. It should be appreciated that the non-contact infrared communication ports can be distributed in any functional manner across the top surface of the bottom unit or bottom surface of the top unit. It should further appreciated that any other communication port or structure known to persons of ordinary skill in the art can be implemented herein.

In one embodiment, the LED receivers are high speed silicon photodiodes with extra fast response times, radiant sensitive area of approximately 0.25 mm$^2$ and an angle of half sensitivity of approximately 15 degrees.

The LED receivers have the following characteristics: a) reverse voltage of approximately 60V, b) power dissipation of approximately 75 mW, c) junction temperature of approximately 100 degrees Celsius, d) an operating temperature range of −40 to 85 degrees Celsius, e) forward voltage of approximately 1V, f) minimum breakdown voltage of 60V, and g) diode capacitance of approximately 1.8 pF.

Referring back to FIGS. 1, 2, and 3, atop the controller unit 101, 201 are handles 211, 311 and a workspace in the form of a useable shelf 112, 212. The handles, located on the upper pumping portion of the system, are directly connected to the internal structure or frame of the system and are not simply an extension of the exterior plastic molding, housing, or skins surrounding the top unit 101, 201. The direct connection to the internal frame of the system permits using the handle to reposition the system in a manner that is safe and can reliably handle the load, particularly when the instrument is in operation with six liters of water (adding approximately 40 lbs).

Figure 5:
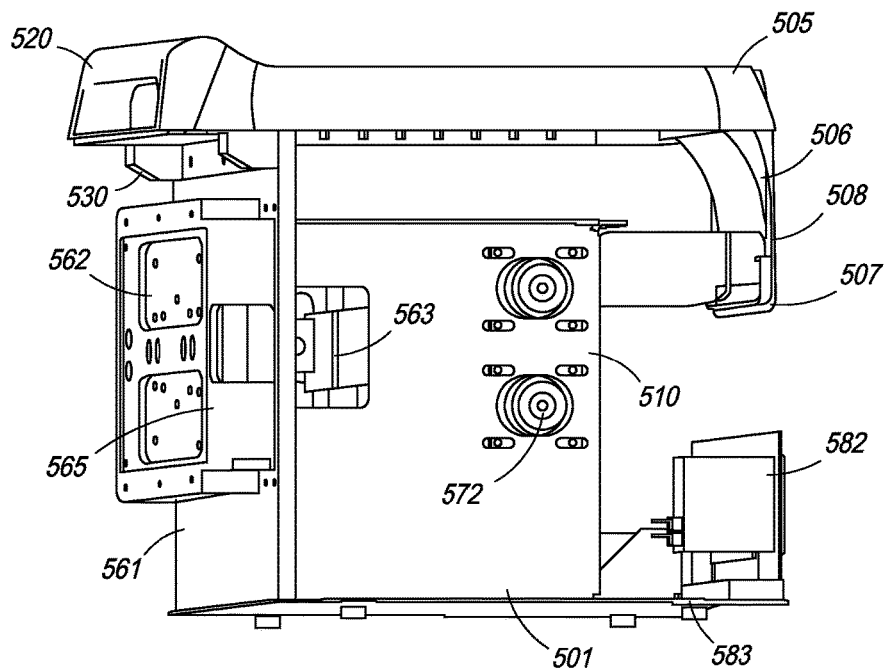
FIG. 5 is a view of the internal structure of the top unit in one embodiment of the present invention.

Referring to FIG. 5, in one embodiment, the top unit 501 comprises an internal metal casing, frame or housing 510 within which, and to which, the electronics, controller, and other top unit components are contained. The internal casing 510 comprises a horizontal protruding arm 507 that extends to the back side of the top unit 501. The substantially horizontal top shelf 505 comprises at least one handle 520 that is integrally formed into the top shelf structure 505, a base bracket 530, and a vertical arm 506, thereby creating a single, contiguous metal or molded plastic piece. The base bracket 530 is securely attached to the internal casing 510 at the front of the top unit 501 and the vertical arm 506 is securely attached to the protruding arm 507 at point 508 using screws. By securely attaching the shelf 505 and handle 520 structure to the internal casing 510 of the top unit 501, one avoids potential damage or breakage that would normally occur by placing large weight loads at the point of connection between a handle and an external or outside housing of the top unit.

Also attached to the internal frame or casing 510 is a metal door 562, with hinges 565, which forms the internal frame of door 110, shown in FIG. 1. Door 562 is securely attached to plate 561 which is part of internal frame 510. Structures 563 and 572 are structures that hold, and/or represents protusions of, the internal motors and pulley assemblies. Protusion 583, which extends from the back of frame 510, is used to connect various electronic components, including a power entry module and USB connections 582.

Figure 12:
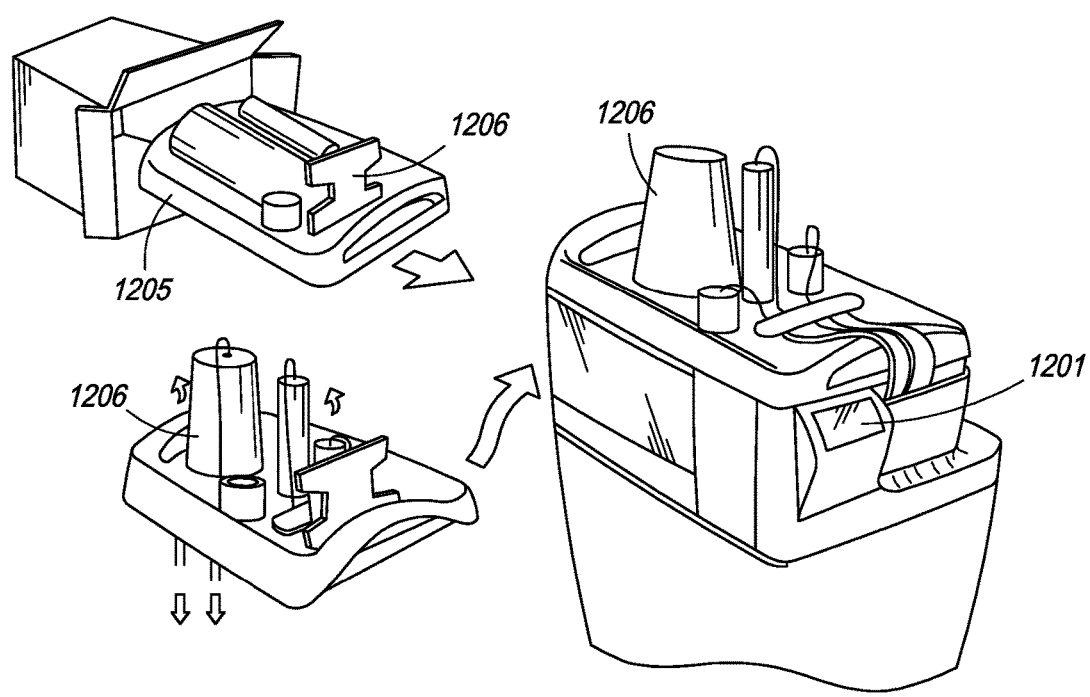
FIG. 12 are drawings depicting the top of the dialysis system with a modular, mobile workspace.

The top of the controller unit, or shelf 505, is flat and has side-walls making it ideal for storage of supplies or a temporary working surface. Referring to FIG. 12, in one embodiment, disposables 1206 for use in the system are shipped in packaging preassembled on a tray 1205. The tray 1205 is placed on top of the controller unit 1201 workspace, thereby permitting easy access to, and management of, the required disposables, which is of particular importance for home users. The controller unit 1201 is waterproof rated, so that, in case of a liquid spill, it should not seep into and damage the top controller unit 1201.

Figure 10:
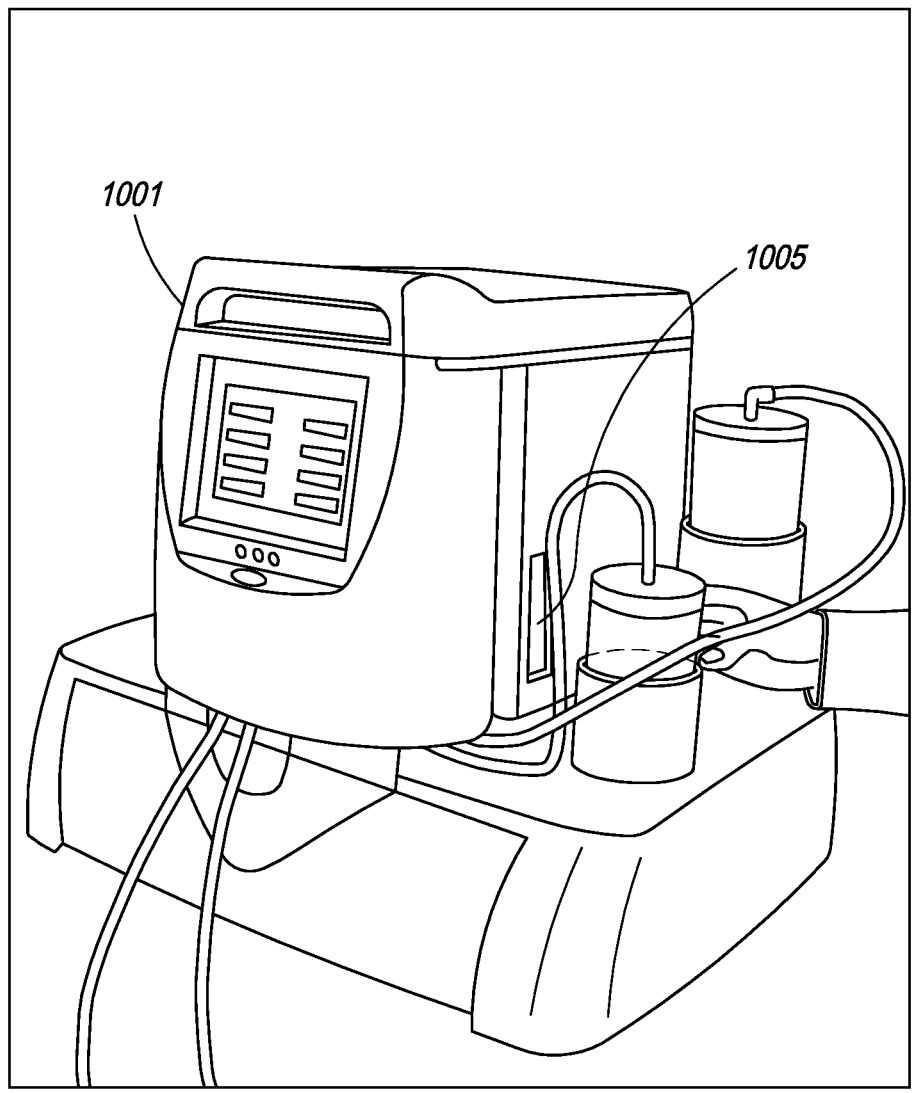
FIG. 10 is a side of an embodiment of the dialysis machine with a bar code reader.

Another structural feature of the controller unit 1001 is shown in FIG. 10. Preferably, the unit 1001 has a built-in exposed reader, such as a bar code reader or RFID tag reader 1005, which can be used to read codes or tags on the disposable components. Operationally, a user would preferably swipe all of the codes/tags on the disposable components by the reader. Prompting the user can be effectuated through an initial GUI dialysis setup step which instructs the user to swipe each disposable component passed the reader.

Upon doing so, the reader obtains identifying information about the disposable, transmits that identifying information to an internal table stored in memory, compares the identifying information to the contents of the internal table, and verifies (or does not verify) that the correct disposable components (particularly additives used in the dialysate) are present. The contents of the internal table can be generated by manual input of the identity and amount of the disposables or by remote access to a prescription that details the identity and amount of the disposables. This verification step has at least two benefits. The first is to ensure that the user has, in his or her possession, all of the required components and the second is to ensure that the correct components are being used (not counterfeit or unsuitable disposables).

In another embodiment, the reader 1005 mounted on the side of the top unit is a specialized multi-function infrared camera that, in one mode, provides the ability to read bar codes and, in another mode, detects a level change in the infusate container. The camera emits an infrared signal that reflects off fluid level. The reflected signal is received by the camera's infrared receiver and processed, using a processor, to determine the location of the meniscus of the fluid level. In one embodiment, the camera can determine and monitor a change in the fluid level to a resolution of 0.02 mm. In one embodiment, the camera is a 1.3 megapixel single-chip camera module with one or more of the following characteristics: a) 1280 H×1024V active pixels, b) 3.0 μm pixel size, c) ⅓ inch optical format, d) RGB Bayer color filter array, e) integrated 10-bit ADC, f) integrated digital image processing functions including defect correction, lens shading correction, image scaling, demosaicing, sharpening, gamma correction, and color space conversion, g) embedded camera controller for automatic exposure control, automatic white balance control, and back level compensation, h) programmable frame rate and output derating functions, i) up to 15 fps SXGA progressive scan, j) low power 30 fps VGA progressive scan, k) 8-bit parallel video interface, l) two-wire serial control interface, m) on-chip PLL, n) analog power supply from 2.4 to 3.0 V, o) separate I/O power supply, p) integrated power management with power switch, and q) 24 pin shield socket options. In one embodiment, the camera is a 1.3 megapixel camera made by ST Microelectronics, Model No. VL6624/V6624.

The top or bottom unit of the dialysis system also preferably has electronic interfaces, such as Ethernet connections or USB ports, to enable a direct connection to a network, thereby facilitating remote prescription verification, compliance vigilance, and other remote servicing operations. The USB ports permit direct connection to accessory products such as blood pressure monitors or hematocrit/saturation monitors. The interfaces are electronically isolated, thereby ensuring patient safety regardless of the quality of the interfacing device.

Figure 8:
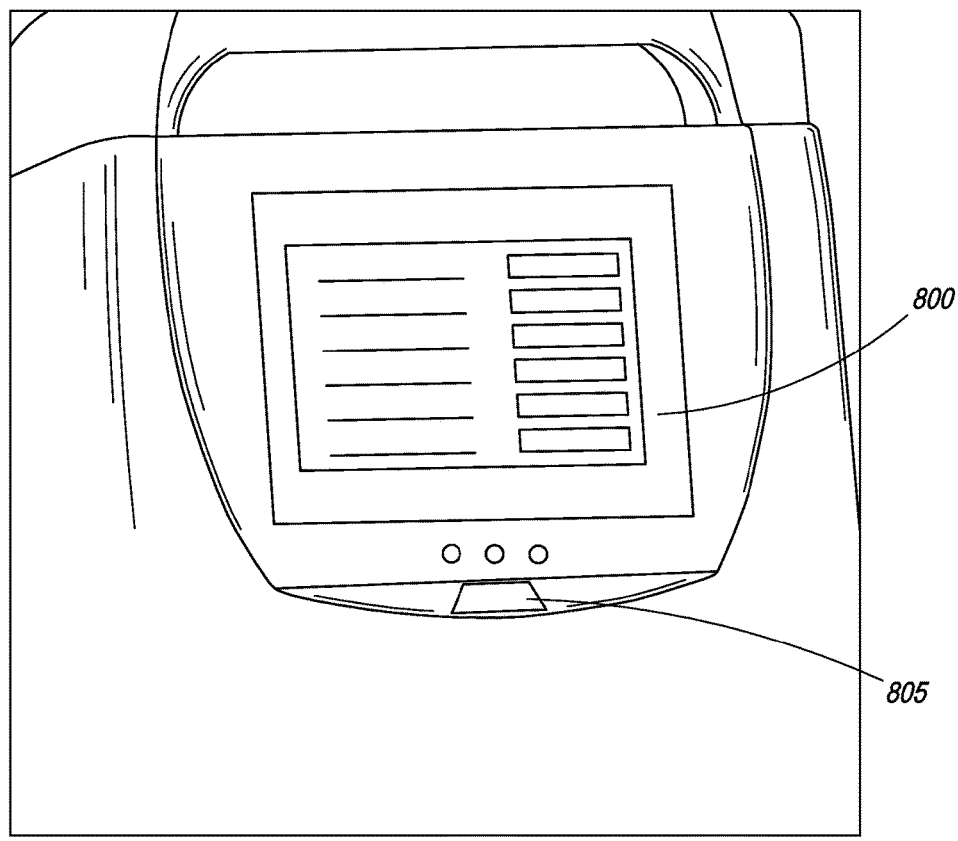
FIG. 8 is a front view of an exemplary graphical user interface implemented in the present invention.

The front of the top unit has a graphical user interface 114 that provides for a simple user interface with the system 100. In a home setting it is important that the device be easy to use. Maximal use of colors and the touch screen is ideally suited for the application. The touch screen allows multiple user input configurations, provides multiple language capability, and can be readily seen at night (particularly with brightness controls and night-vision colors). The GUI further includes a feature for the automatic closing, opening, and locking of the door during operation. In one embodiment, the GUI opens the door to a first latch position and then a user must press a physical door-open button to fully open the door. In another embodiment, the device has a manual override which permits the user to open the door (e.g. by pressing the open door button twice or with extra force) to manually open the door. Referring to FIG. 8, preferably, proximate to the GUI 800, is a single mechanical button 805, with lighted visual indication, that, if activated, provides a central stop button with a common function (such as stopping the system) regardless of the state of operation.

Figure 6:
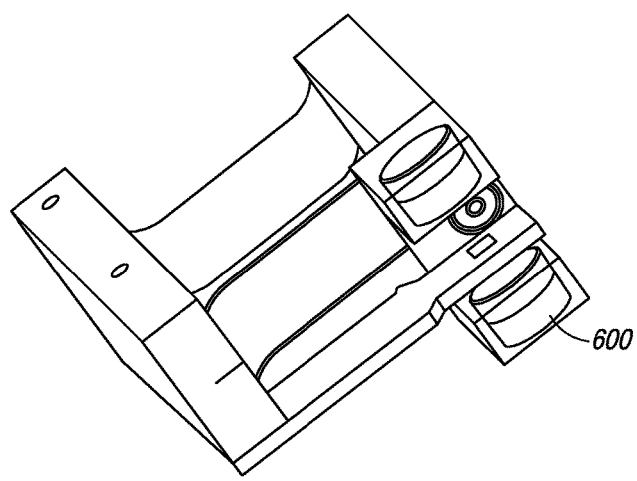
FIG. 6 is a drawing of a component in a scale-based fluid balance implemented in the present invention.
Figure 7A:
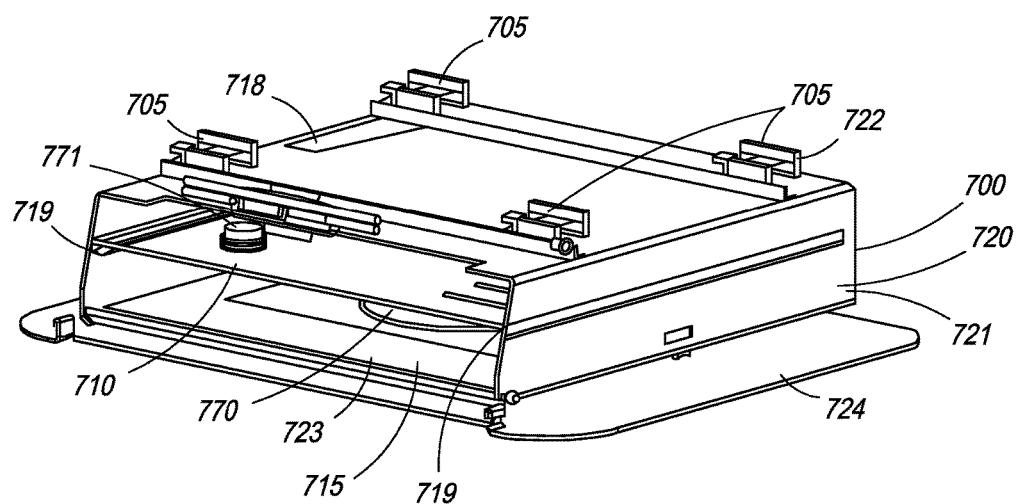
FIG. 7a is a side perspective view of a reservoir with an integrated scale.
Figure 7B:
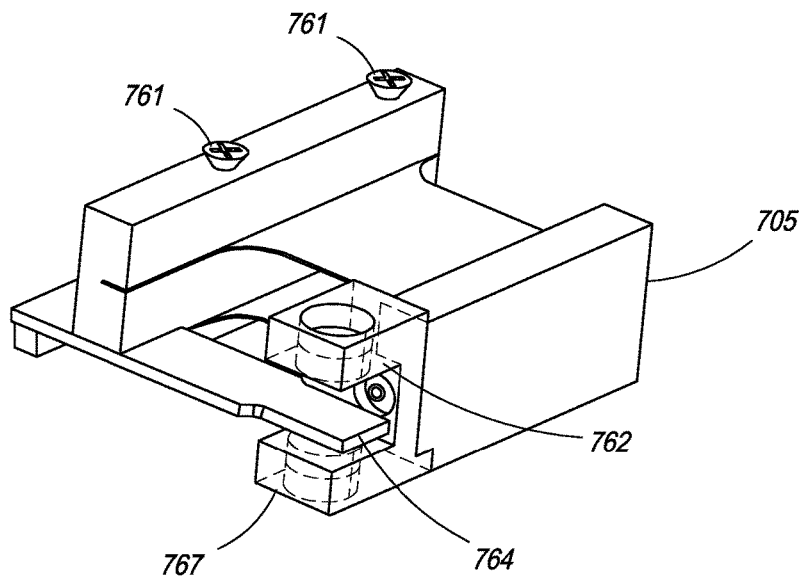
FIG. 7b is a side perspective view of a flexure assembly.

Referring to FIG. 1, the reservoir system 102 has a door 118 which, when pulled, slides the reservoir 122 out to permit access to the reservoir. The reservoir volume is monitored by a scale system. The scale-based fluid balance 600, depicted in FIG. 6 and more particularly in FIGS. 7a and 7b, is integrally formed with the reservoir and provides accurate fluid removal data and enables accurate balance calculations, thereby preventing hypotension and other ailments caused from fluid imbalances. Integrating the scale with the reservoir and enclosing them completely provides for a more robust system.

Referring to FIG. 7a, the internal structure 700 of the reservoir system is shown. A metallic internal frame 720 comprises two sides 721, a back 722, and open faced front 723, and a base 724. The internal structure or frame is shown without the external housing, as depicted as element 102 in FIG. 1. A scale 718 is integrated into the reservoir internal structure 700. The bottom surface 715 of the scale 718 comprises a metal surface or pan that, together with the rest of the scale 718, is suspended from the external reservoir housing (shown as 102 in FIG. 1) by four flexures 705. Below the bottom surface 715 of the scale is preferably situated a heating pad, such as a square, rectangular, circular, or other shaped surface capable of incurring a temperature increase and conducting the increased temperature, as heat, to surface 715. A conductivity coil 770, capable of exerting a field and using changes in that field to measure conductivity, is integrated into base surface 715. Accordingly, when a reservoir bag (not shown) is placed on bottom surface 715, it can be heated by a heating pad and, because it is in contact with coil 770, its conductivity can be monitored.

The internal surfaces of the sides 721 comprise a plurality of rails, elongated members, or protusions 719 that serve to secure, hold, encase or attach to a disposable reservoir bag mounting surface, such as a plastic sheet, 710 to which a reservoir bag can be attached. Specifically, a reservoir bag positioned on surface 715 can have an outlet attached to conduit 771 integrated into sheet 710. Mounted in each of the four corners of the scale surface 718 are flexures 705 with each one comprising a hall sensor and magnet.

Referring to FIG. 7b, the flexure 705 comprises a plurality of attachment points 761 where the flexure is secured to the external reservoir housing. The flexure further comprises magnetic bodies 762, such as two magnets, and a hall sensor 764. The base 767 of the flexure 705 is attached to the top surface 715 of scale 718. As the scale 718 displaces due to the application of a weight load (e.g. when the reservoir bag fills with dialysate the bag presses on surface 715, thereby pulling scale 718 downward), the flexure 705, which is connected to the scale at one end and the external housing at another end, will flex and the magnet 762, mounted on the one end of the flexure 705, will track that change by virtue of changes to the magnetic field generated by the magnetic body 762. The hall sensor 764 detects changes in the magnetic field strength. One of ordinary skill in the art would understand how to translate this sensed magnetic field change into a measure of the applied weight load.

The placement of disposable components, such as the dialyzer 103, sorbent cartridge 107, and infusate, in a manner that is external to the system but easily accessible permits the use of multiple sized sorbent cartridges, dialyzers, and infusate mixes, thereby giving greater flexibility to the use and applicability of the system. Referring to FIGS. 3, and 9, the disposable components, particularly the fully disposable blood and dialysate circuits, are prepackaged in a kit (which includes dialyzer, manifold, tubing, reservoir bag, ammonia sensor, and other components) and then used by opening the front door 303 of the top unit 301 (as discussed above), installing the dialyzer 313 and installing the manifold 304 in a manner that ensures alignment against non-disposable components such as pressure, sensors, and other components. A plurality of pump shoes 305 integrated into the internal surface of the front door 303 makes loading of disposable components easy. The manifold only needs to be inserted and no pump tubing needs to be threaded between the rollers and shoes 305. This packaged, simple approach enables easy disposables loading and cleaning of the system. It also ensures that the flow circuitry, shown in FIG. 11, is properly configured and ready for use. In operation, the top unit 301 is attached to the bottom unit 302 with reservoir 322.

The front door opens widely (approximately 100 degrees), for loading the disposables. Having a wide opening facilitates manifold loading and easy cleaning of the faces of the machine and inside of the door. Having the door close and cover the moving parts of the device makes it safer and more robust, which is particularly important for home use. Additionally, having the front door house the display saves space and re-enforces the important point that the device is not to be operated unless the disposables are in place and the door is closed. The door provides the necessary occlusion force on the manifold and its pump segments. The door also contains a touch screen, audio alarm, and manual stop button in the face of the door.

In one embodiment, the door is held in a fully closed position by an electric stepper motor. This motor is operated via the user interface and, in particular, by a user pressing a button when the door is ready to be fully closed or opened. To ensure proper pressure is placed on the manifold structures by the door and pump shoes, it is preferred to have an electronic mechanism by which the door is closed and sufficient closing door force is generated. In one embodiment, a closing door force of 90 to 110 lbs is generated.

Figure 11A:
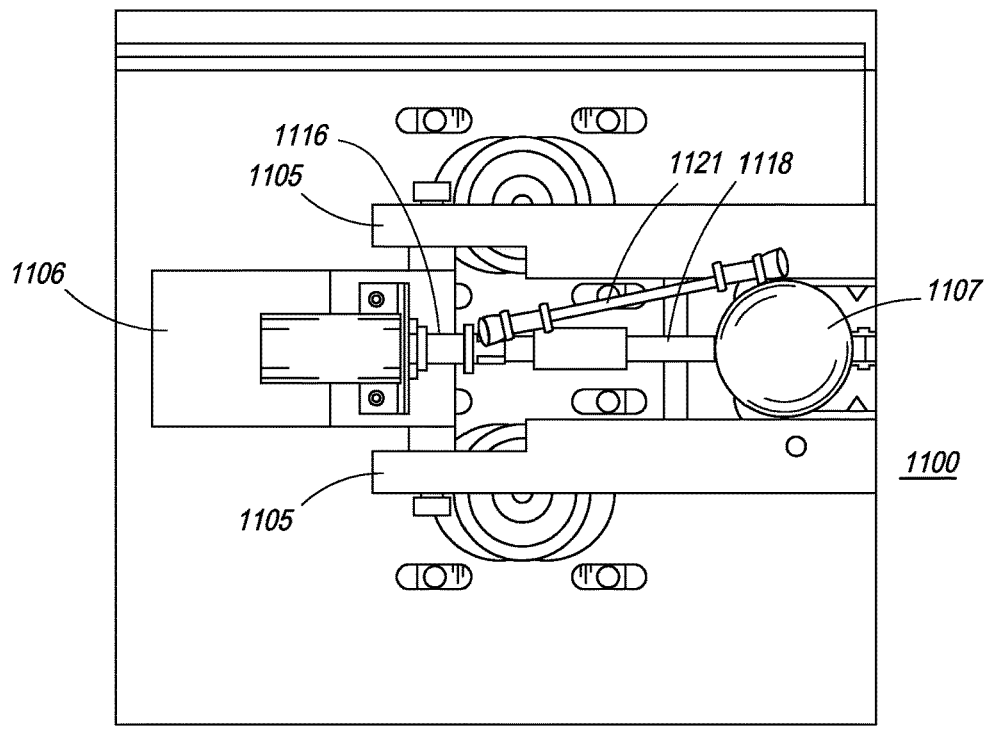
FIG. 11a is schematic of one embodiment of the door assembly.

Referring to FIG. 11*a*, one embodiment of the power door closing mechanism 1100 is shown. A stepper motor 1106 is mechanically engaged with a lead screw 1116, such that, when actuated by a controller, the stepper motor 1106 causes the lead screw 1116 to turn and, consequently, to cause rod 1118 to apply a motive force to a hook. The hook, located under member 1140, serves to latch onto U-latch 1130 and, when pulled, turned, or otherwise moved inward toward stepper motor 1106, pull the U-latch 1130 further closed, thereby applying the requisite closing door force. The hook is physically engaged with rod 1118 and can be manipulated to pull the U-latch 1130 tightly closed or to loosely engage with the U-latch 1130. The power closing system is mounted and kept in proper orientation by mounting brackets 1105.

Figure 4:
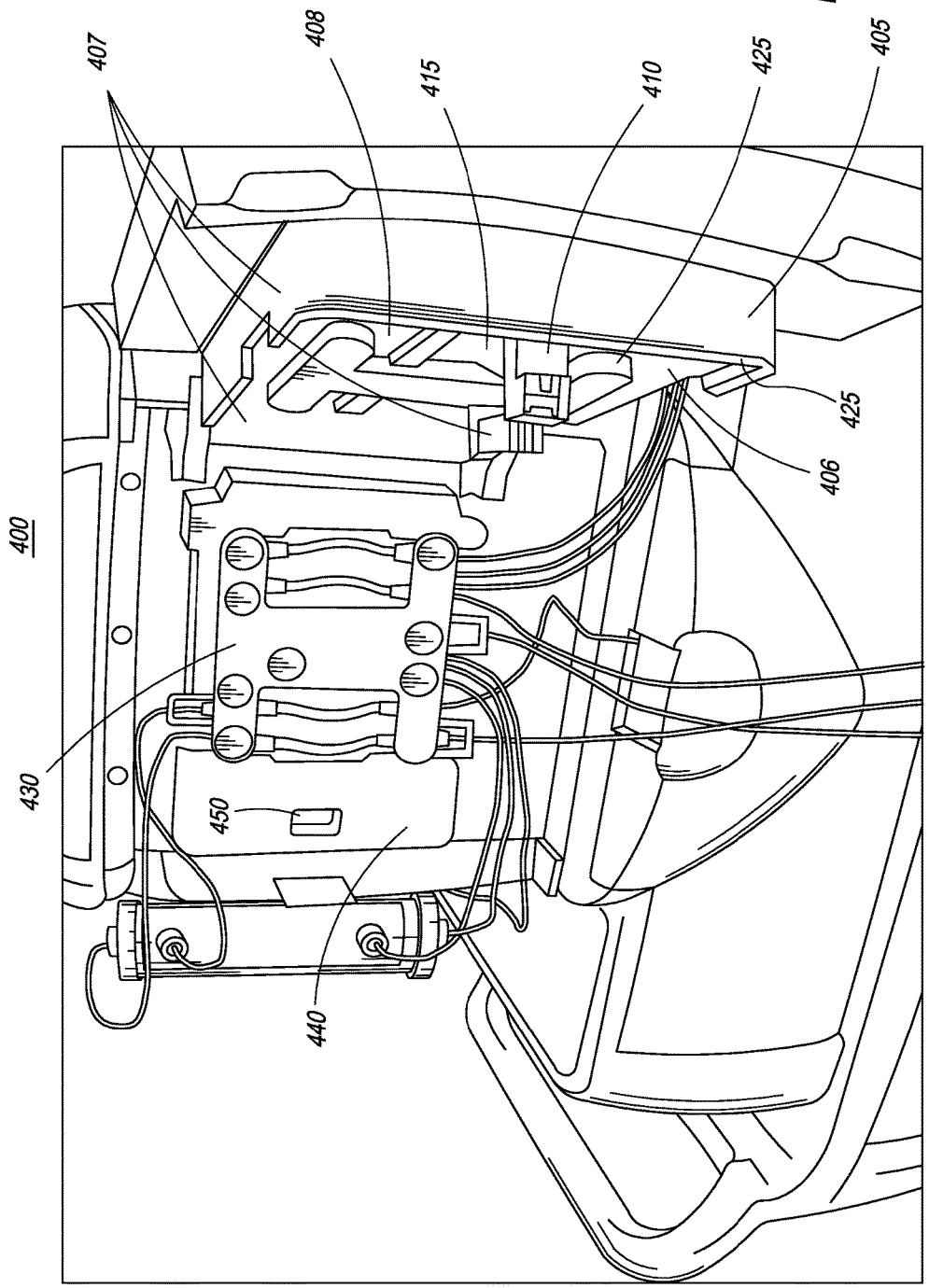
FIG. 4 is a front view of one embodiment of the dialysis system with an open door and U-shaped latch.

Operationally, a user closes the door sufficiently to engage the U-latch 410 on the door with the hook 450 inside the internal volume of the controller unit, as shown in FIG. 4. A user then indicates to the portable dialysis machine a desire to close the door, preferably through a mechanical button or graphical user interface icon, which, when pressed, sends a signal to a controller that, in turn, actuates the stepper motor 1106. The stepper motor 1106 applies a motive force to the hook 450, which then pulls the engaged U-latch 1130, 410 tightly closed. In one embodiment, a controller monitors the torque force being applied by the motor and, when it reaches a pre-defined limit, deactivates the stepper motor. In another embodiment, a hall device positioned proximate to the lead screw senses the extension of the lead screw and determines the extent of movement of the screw. If the screw has sufficiently moved in the direction of creating greater closing door force, the hall sensor transmits a signal to the controller to deactivate the motor. Alternatively, the sensor constantly transmits a signal indicative of the extension of the screw, which is then interpreted by the controller to determine if sufficient motive force has been applied, and whether the stepper motor should be deactivated. In any of these embodiments, if the motor over torques, a pre-set distance is exceeded, or the door does not reach its fully closed position in a predetermined time, a controller can actuate the motor to stop and reverse to a fully open state. The controller can also cause a visual and/or auditory alarm to sound.

When a user wishes to open the door, a mechanical button or graphical user interface icon is activated, sends a signal to a controller that, in turn, actuates the stepper motor 1106 in reverse. The hook then becomes loosely engaged with the U-shaped latch. A mechanical release button 1107 is then pressed to disengage the loosely engaged hook from the U-shaped latch.

In addition to providing the requisite closing force, this power door closing mechanism has several important features. First, it is designed to avoid obstructions from being caught in the door and subject to the powerful door closing force. Referring to FIG. 4, the manifold is surrounded by an edge guard which prevents a door latch from engaging with a latch receiver on the top unit if a blockage, such as person's finger or improperly installed disposable, is between the door and the top unit's base plate. Door 405 comprises an internal surface 406 to which a metallic casing 425 is attached. In one embodiment, the top surface of the internal surface 406 of the door 405 is securely attached to an external surface of the casing 425. The casing 425 is substantially rectangular and defines a cavity with four sides 407 and a base 408 creating an internal volume. The cavity opens toward the manifold structure 430 of the dialysis system 400 and encompasses and surrounds the manifold structure 430 and guard 440, which is preferably a plastic shroud that surrounds the manifold structure 430 at its top and sides. Attached to the surface of the base 408 are the pump shoes 415 and at least one U-shaped latch 410, which protrudes toward the back plate. Integrated within, and extending out of, the guard is a hook 450 which is configured to securely engage and disengage the U-shaped latch 410. If the door is correctly closed and nothing is caught between the door and the guard, then the U-shaped latch will be mechanically hooked by the power-door lock hook mechanism. If an obstruction is in the door pathway, the metal casing 425 will be unable to extend into the internal volume of the top unit (and encompass the guard) and, therefore, the U-shaped latch will be unable to engage the hook, thereby preventing the mechanical hooking and accidental power closing of the door when an obstruction is in place.

Figure 11B:
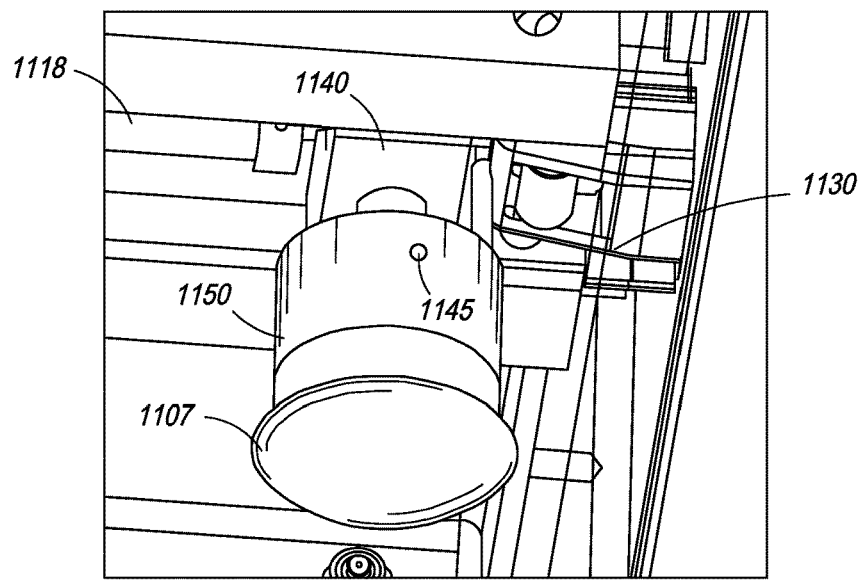
FIG. 11b is a schematic of one embodiment of the door release.

Second, the mechanical button release 1107 can only be actuated when the power closing door force has been dissipated through the reverse motion of the stepper motor, thereby preventing an accidental release of, and rapid opening of, the door. Referring to FIGS. 11*a* and 11*b*, when the door is closed and locked, a collar 1150 on the button shaft 1107 turns 90 degrees moving a push pin away from the power-door locking hook. The collar 1150 is turned by virtue of rod 1121, which is connected to the collar at point 1145 and in mechanical engagement with lead screw 1116. The collar 1150 is spring loaded and locked by a small pin solenoid. If the user presses the button when in the locked position the button will move into the machine but, because of the displacement caused by the turning of the collar, will not disengage the hook, thereby preventing the door from opening. If the power is lost or unintentionally terminated, then the pin solenoid will release, allowing the collar to turn back 90 degrees and placing the push-pin in proper alignment. Then when the user presses the button the push pin will contact the power-door hook and release the door latch. This mechanism provides the convenience and safety back up of a mechanical door release without concern that the mechanical door release can accidentally be activated to cause the door to swing open with tremendous force. It should be appreciated that the term "hook" or "latch" should be broadly defined as any protusion or member capable of physically or mechanically engaging with another protusion or member. It should further be appreciated that the term "U-shaped latch" is not limiting and any latching or hooking mechanism, as defined above, can be used.

As discussed above, shelving space formed by the bottom unit and surrounding the top unit employs drainage paths with fluid sensors, in multiple locations internal and external to the device, in order to enable zoned leak detection. Specifically, by building in drainage paths, with optical leak sensors, into the external body of the device, the system captures and routes fluids potentially leaked from the external components (like the sorbent canister) to the optical leak sensors.

Figure 9A:
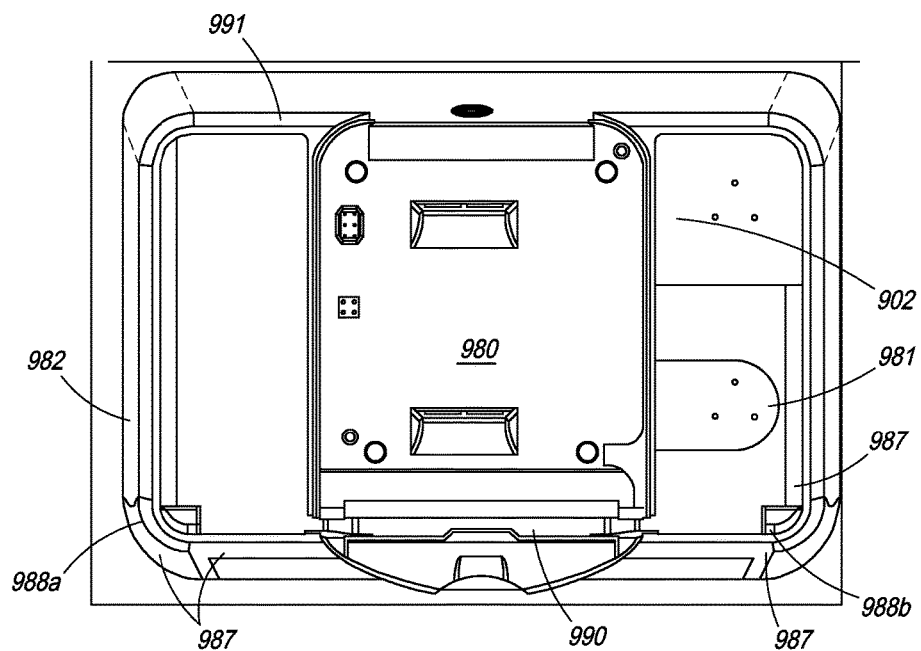
FIG. 9a is a first view of the top surface of the bottom unit with leak channels and leak detectors designated therein.

In one embodiment, integrated within the external housings of the bottom unit are at least three different optical leak detectors. Referring to FIG. 9*a*, the top surface of bottom unit 902 is slightly angled, with center 980 raised relative to sides 981 and 982. In one embodiment, the surface tilts downward, from center area 980 to sides 981 and 982, by an angle of 1 to 10 degrees, preferably 3 degrees. Channels 987 encircle the top surface of the bottom unit, extend around the periphery, extend through the center of the top surface, and/or extend through any other portion of the top surface. By virtue of the angled top surface of the bottom unit 902, the channels 987 are also angled from the center 980 to the sides 981, 982. In another embodiment, the top surface is also slightly angled downward from back side 991 to front surface 990. The angled channels 987 cause fluids to be directed away from the center and/or back of the system forward and to the sides where leak detectors 988 are positioned and are in fluid communication with the channels 987.

Figure 9B:
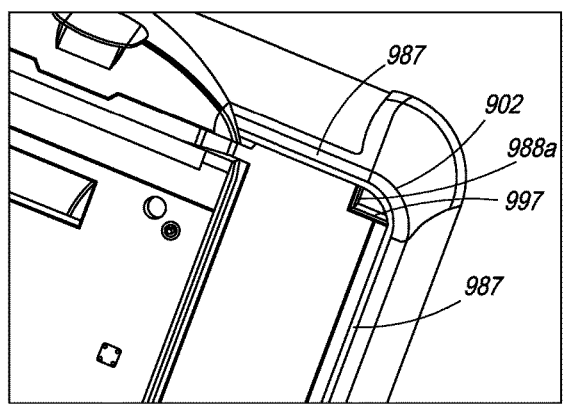
FIG. 9b is a second view of the top surface of the bottom unit with leak channels and leak detectors designated therein.

A first optical leak detector 988a is located on the front right corner of the top surface of the bottom unit 902. A second optical leak detector 988b is located on the front left corner of the top surface of the bottom unit 902. Each leak detector is positioned within a well or cavity and comprises an optical sensor, which is located in the side of the well. The optical sensor detects fluids that have drained and/or been channeled to the wells and transmits a detected signal to a controller in the top unit. The detected signal is processed by a processor determine if a leak has occurred. Detected signals are then stored and, if required, the processor causes an alarm or alert to display on the GUI. The well or cavity preferably comprises a rounded base to permit the user to easily wipe the well dry. FIG. 9b shows a more detailed view of the top surface of the bottom unit 902 with channels 987 and leak detector 988a positioned within well 997.

Figure 9C:
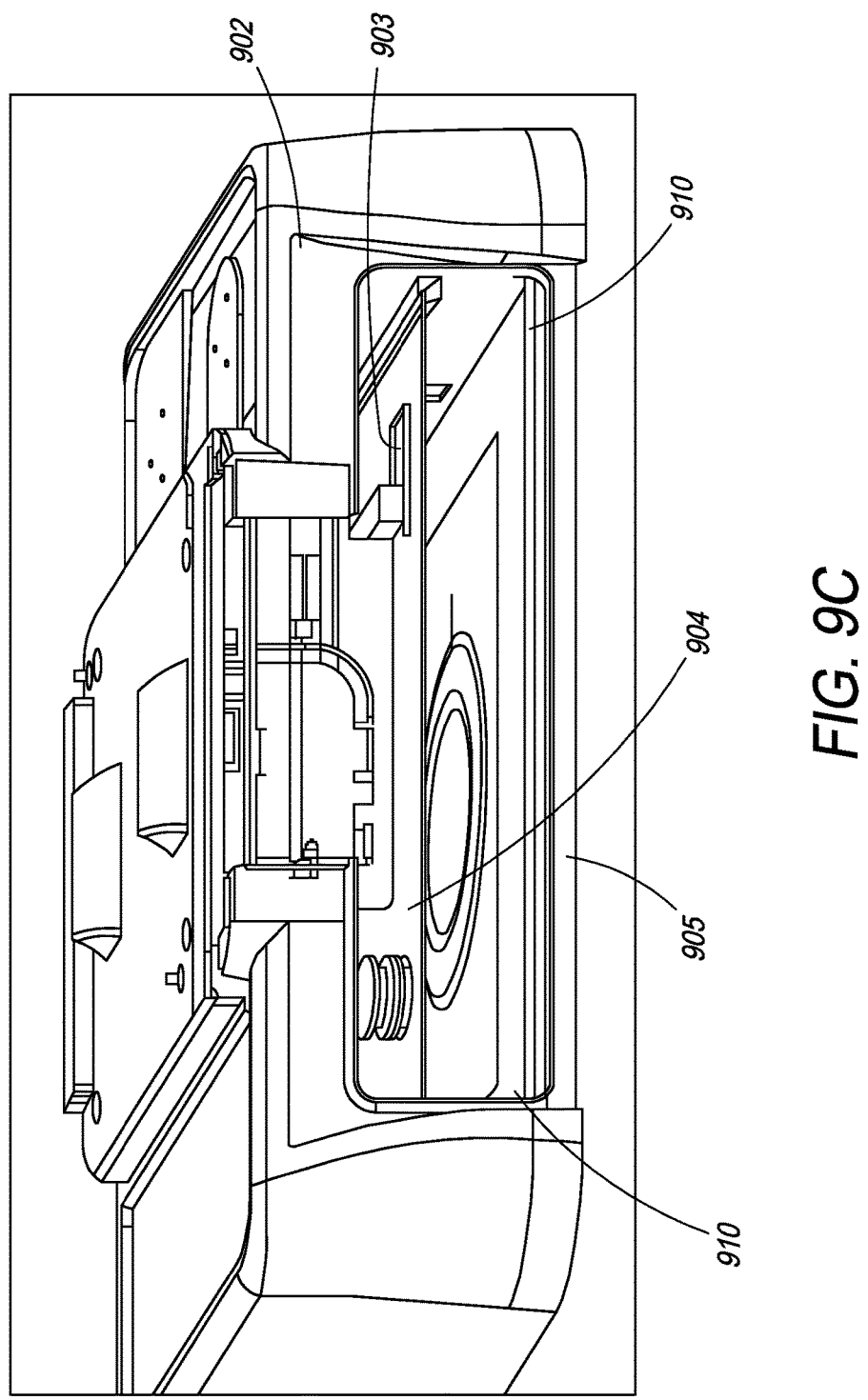
FIG. 9c is a front view of the bottom unit with leak channels and leak detectors designated therein.

Referring to FIG. 9c, at least one additional leak detector is located within the bottom unit 902 and, more particularly inside the reservoir 903, within which a scale 904 is integrated. Channels 905 are integrated into the reservoir structure, such as the internal housing or metal bag holder, and are preferably angled, from one side to the other side or from the center to either side. In one embodiment, the angle is in the range of 1 to 10 degrees and more particularly 3 degrees. A well 910 housing a leak detector is integrated into the reservoir housing and in fluid communication with the channels 905 in one or both sides of the reservoir housing. If a leak occurs in the disposable bag, fluid will drain to the corner of the metal pan or reservoir housing via channels 905 and be directed into at least one well with a leak sensor 910.

The drainage paths serve two functions: a) to make sure fluid does not enter the instrument and b) to make sure that a leak is quickly contained and routed to a sensor which can trigger an alert or alarm. Additionally, the device preferably also includes fluid drainage channels leading to wells with optical sensors on the interior of the device. So for instance if there is a leak in the internal reservoir the fluid is routed away from critical components and an optical sensor warns of the leak. Based on the sensor activated, the GUI can present an alarm to the user and can specifically identify the location of the fluid leak. By providing several independent zones of leak detection (several fluid sensors and drainage paths), the instrument can guide the user to find the leak quickly. Having multiple channels and sensors allows the system to partially, automatically, identify the source of the leak and offer graphic assistance, toward remedy of the problem, to the user.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

We claim:

1. A modular dialysis system comprising: a controller unit having a first external housing with a front side, a back side, a left side, a right side, a top side and a bottom side, wherein said front side comprises a door configured to provide access to an internal volume within said controller unit and wherein said bottom side comprises a first latch member and a first data transceiver; a reservoir unit having a second external housing with a front side, a back side, a left side, a right side, a top side and a bottom side, wherein said front side comprises a door configured to provide access to an internal volume within said reservoir unit, wherein said top side comprises a second latch member adapted to mate to said first latch member and a second data transceiver, and wherein when said first external housing is securely and removably attached to said second external housing using said first latch member and said second latch member, the first data transceiver is automatically placed in data communication with said second data transceiver, wherein the internal volume within said controller unit houses a manifold and a guard encircling the manifold, wherein the door configured to provide access to the internal volume within said controller unit has an internal surface and wherein said internal surface comprises a plurality of pump shoes, a latch, and casing with sides that protrude into said internal volume when said door is closed.

2. The modular dialysis system of claim 1 wherein, when the door is closed, said latch mechanically engages said hook.

3. The modular dialysis system of claim 2 further comprising a controller configured to actuate a motor to apply a motive force to said door and wherein said application of motive force causes said door to be closed with a force in a range of 90 to 110 lbs.

4. The modular dialysis system of claim 3 further comprising a mechanical release button having a first state and a second state, wherein, in said first state, the button is capable of mechanically engaging a hook connected to said door and wherein, in said second state, the button is not capable of mechanically engaging said hook.

5. A modular dialysis system comprising:
a controller unit having a first external housing with a front side, a back side, a left side, a right side, a top side and a bottom side, wherein said front side comprises a door configured to provide access to an internal volume within said controller unit and wherein said bottom side comprises a first latch member and a first data transceiver;
a reservoir unit having a second external housing with a front side, a back side, a left side, a right side, a top side and a bottom side, wherein said front side comprises a door configured to provide access to an internal volume within said reservoir unit, wherein said top side has an angled surface with a plurality of channels in fluid communication with at least one leak detector and wherein said top side comprises a second latch member adapted to mate to said first latch member and a second data transceiver; and
wherein said bottom side of the first external housing is adapted to securely and removably attach to said top side of the second external housing and when said first external housing is securely and removably attached to said second external housing using said first latch member and said second latch member, the first data transceiver is automatically placed in data communication with said second data transceiver.

6. The modular dialysis system of claim 5 wherein the bottom side of the first external housing comprises an electrical contact pad and wherein the top side of the second external housing comprises a plurality of electrical pins.

7. The modular dialysis system of claim 6 wherein the controller unit is automatically placed in electrical communication with said reservoir unit when the contact pad is aligned and placed in electrical communication with the plurality of push-pins.

8. The modular dialysis system of claim 5 wherein the first data receiver comprises at least one LED transmitter and at least one LED receiver and wherein the second data receiver comprises at least one LED transmitter and at least one LED receiver.

9. The modular dialysis system of claim 5 wherein the internal volume within said controller unit houses a hook and wherein the door configured to provide access to the internal volume within said controller unit has an internal surface that comprises a latch.

10. The modular dialysis system of claim 9 further comprising a controller configured to actuate a motor to apply a motive force to said hook in response to a user input and wherein said application of motive force causes said door to be closed with a force in a range of 90 to 110 lbs.

11. The modular dialysis system of claim 10 further comprising a mechanical release button having a first state and a second state, wherein, in said first state, the button is capable of mechanically engaging said hook and wherein, in said second state, the button is not capable of mechanically engaging said hook.

\* \* \* \* \*